(12) United States Patent
Baraldi et al.

(10) Patent No.: US 7,691,825 B2
(45) Date of Patent: Apr. 6, 2010

(54) ADENOSINE A$_{2B}$ RECEPTOR AGONISTS

(75) Inventors: Pier Giovanni Baraldi, Ferrara (IT); Pier Andrea Borea, Ferrara (IT); Allan R. Moorman, Durham, NC (US); Delia Preti, Ferrara (IT)

(73) Assignee: King Pharmaceuticals Research and Development, Inc., Cary, NC (US)

( * ) Notice: Subject to any disclaimer, the term of this patent is extended or adjusted under 35 U.S.C. 154(b) by 393 days.

(21) Appl. No.: 11/757,559

(22) Filed: Jun. 4, 2007

(65) Prior Publication Data
US 2007/0281902 A1 Dec. 6, 2007

Related U.S. Application Data

(60) Provisional application No. 60/811,350, filed on Jun. 6, 2006.

(51) Int. Cl.
*A61K 31/70* (2006.01)
*C07H 19/167* (2006.01)

(52) U.S. Cl. .................. 514/46; 536/27.23; 536/27.62; 536/27.63

(58) Field of Classification Search ........................ None
See application file for complete search history.

(56) References Cited

U.S. PATENT DOCUMENTS

| | | | |
|---|---|---|---|
| 5,604,210 A | 2/1997 | Nagaoka et al. | |
| 7,144,872 B2 * | 12/2006 | Zablocki et al. | 514/46 |
| 7,427,606 B2 * | 9/2008 | Linden et al. | 514/46 |

* cited by examiner

*Primary Examiner*—Lawrence E Crane
(74) *Attorney, Agent, or Firm*—Paivi Kukkola

(57) ABSTRACT

The present invention provides compounds of the formula

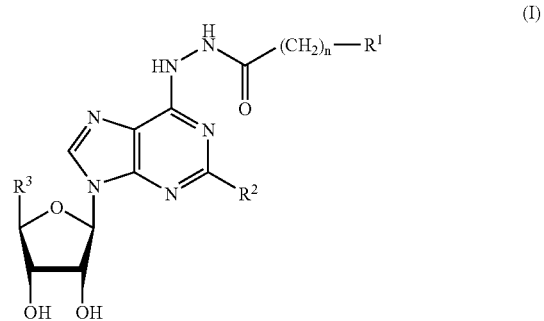

(I)

wherein $R^1$, $R^2$, $R^3$ and n have meaning as described in the specification, methods for their preparation, and pharmaceutical compositions containing them. The compounds of formula (I) are adenosine $A_{2B}$ receptor agonists and, thus, may be employed for the treatment of diseases in mammals that are mediated by the $A_{2B}$ receptor including, but not limited to, septic shock, cystic fibrosis, impotence, diarrhea, and cardiac diseases. Cardiac diseases include hyperplasia consequent to hypertension, arteriosclerosis, and heart attack. The present invention also provides methods for the induction of pharmacological stress to facilitate coronary imaging of areas of ischemia by employing compounds of formula (I). The compounds of formula (I) may be labeled, e.g., with radioactive isotopes, and therefore are useful in kinetic binding experiments.

11 Claims, No Drawings

ADENOSINE $A_{2B}$ RECEPTOR AGONISTS

This application claims the benefit of U.S. Provisional Application No. 60/811,350, filed Jun. 6, 2006 incorporated herein by reference in its entirety.

The present invention relates to novel adenosine $A_{2B}$ receptor, agonists, pharmaceutical compositions containing them, and to methods of treating conditions and diseases mediated by the adenosine $A_{2B}$ receptor activity, by employing such compounds.

Accordingly, the present invention provides compounds of the formula

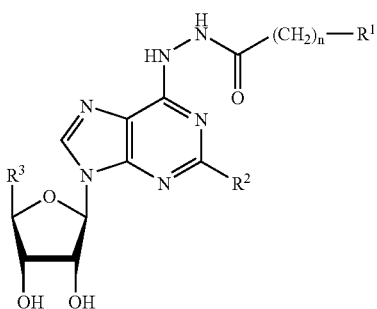

(I)

wherein
$R^1$ is an optionally substituted aryl or heteroaryl;
n is zero or 1;
$R^2$ is H or halogen;
$R^3$ is $CH_2OR^4$ in which
$R^4$ is H or $C_1$-$C_6$ alkyl provided $R^4$ is not H when n is zero and $R^1$ is unsubstituted phenyl; or
$R^3$ is C(O)NH—$R^5$ in which
$R^5$ is $C_1$-$C_6$ alkyl or
$R^3$ is

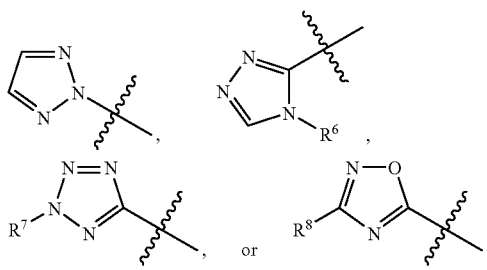

in which
$R^6$, $R^7$, and $R^8$ are H or $C_1$-$C_6$ alkyl;
or a pharmaceutically acceptable salt thereof.

The present invention encompasses the pharmaceutically acceptable salts of the above-described compounds, and pharmaceutical compositions containing the above-described compounds or their salts, as the active ingredient.

The compounds of the present invention are adenosine $A_{2B}$ receptor agonists and, thus, may be employed for the treatment of diseases in mammals that are mediated by the $A_{2B}$ receptor including, but not limited to, septic shock, cystic fibrosis, impotence, diarrhea, and cardiac diseases, as described, e.g., by Rivkees et al. in *Mol. Endocrinol.* 1992, 6, 1598-1604; Le Vraux et al., in *Life Sci.* 1993, 52, 1917-1924; Chiang et al. in *Br. J. Clin. Pharmacol.* 1994, 38, 357-362; Hancock et al in *Br. J. Pharmacol* 1995, 114, 152-166; Feoktistov et al. in *Pharmacol. Rev.* 1997, 49, 381-402; Dubey et al. in *Hypertension* 1998, 31, 516-521; Clancy et al. in *Cell. Physiol.* 1999, 45, 361-369; Peyot et al. in *Circ. Res.* 2000, 86, 76-85; and Volpini et al in *Curr. Top. Med. Chem.* 2003, 3, 427-443. Cardiac diseases include hyperplasia consequent to hypertension, arteriosclerosis, and heart attack.

Listed below are definitions of various terms used to describe the compounds of the present invention. These definitions apply to the terms as they are used throughout the specification unless they are otherwise limited in specific instances either individually or as part of a larger group.

As used herein, the term "agonist" refers to any ligand that binds to receptors and thereby alters the proportion of them that are in an active form, resulting in a biological response.

As used herein, the term "optionally substituted aryl" refers to an unsaturated aromatic carbocyclic group of from 6 to 14 carbon atoms having a single ring, i.e., monocyclic aryl, e.g., phenyl, or multiple condensed (fused) rings, e.g., naphthyl or anthryl. Preferred aryls include phenyl, naphthyl and the like. Six-membered rings are highly preferred Such aryl groups may optionally be substituted with from 1 to 5 substituents and preferably 1 to 3 substituents selected from the group consisting of hydroxy, acyl, optionally substituted alkyl, alkoxy, alkylthio, alkenyl, alkynyl, optionally substituted amino, acyloxy, acylamino, aryl, aralkyl, aryloxy, azido, carboxy, cyano, halo, nitro, heteroaryl, heteroaryloxy, trihalomethoxy, dihalomethyl, trihalomethyl, perhaloalkyl. Preferred substituents include alkyl, alkoxy, halo, cyano, and trihalomethyl.

The term "monocyclic aryl" refers to optionally substituted phenyl as described above under aryl. Preferably, the monocyclic aryl is substituted by 1 to 3 substituents selected from the group consisting of halogen, cyano, or trifluoromethyl.

As used herein, the term "aryloxy" refers to optionally substituted aryl-O.

As used herein, the term "arylthio" refers to optionally substituted aryl-S.

As used herein, the term "aryloxycarbonyl" refer s to aryloxy-C(O).

As used herein, the term "heterocyclyl" or "heterocyclic" refers to a monovalent saturated or unsaturated group having a single ring or multiple condensed rings, from 1 to 15 carbon atoms and from 1 to 4 hetero atoms selected from the group consisting of nitrogen, sulfur and oxygen within the ring. Unless otherwise constrained by the definition for the heterocyclic substituent, such heterocyclic groups can be optionally substituted with 1 to 5 substituents selected from the group consisting of optionally substituted alkyl, optionally substituted alkoxy, aryl, aryloxy, halo, nitro, heteroaryl, thiol, optionally substituted alkylthio, arylthio, trihalomethyl, and the like. Such heterocyclic groups can have a single ring or multiple condensed rings.

The term "heteroaryl" refers to an aromatic heterocycle, e.g., 5- to 6-membered monocyclic aromatic group comprising from 1 to 2 hetero atoms selected from the group consisting of nitrogen, sulfur and oxygen Furan and thiophene are preferred.

Such heteroaryl groups may be optionally substituted with from 1 to 5 substituents and preferably 1 to 3 substituents selected from the group consisting of hydroxy, acyl, optionally substituted alkyl, alkoxy, alkylthio alkenyl, alkynyl, optionally substituted amino, acyloxy, acylamino, aralkyl, aryloxy, azido, carboxy, cyano, halo, nitro, heteroaryl, heteroaryloxy, trihalomethoxy, dihalomethyl, perhaloalkyl, and trihalomethyl. Preferred substituents include alkyl, alkoxy, halo, cyano, nitro, trihalomethyl, and alkylthio. Such heteroaryl groups can have a single ring (e g, pyridyl or furyl) or multiple condensed rings (e.g., indolizinyl or benzothienyl).

As used herein, the term "heteroaryloxy" refers to optionally substituted heteroaryl-O.

As used herein, the term "heteroaryloxycarbonyl" refers to heteroaryloxy-C(O).

As used herein, the term "acyl" refers to optionally substituted alkyl-C(O)—, optionally substituted aryl-C(O), or optionally substituted heteroaryl-C(O).

As used herein, the term "acyloxy" refers to acyl-O.

As used herein, the term "acylamino" refers to acyl-N, wherein the N may be optionally substituted by an alkyl, aryl, heteroaryl, or sulfonyl group or hydrogen.

As used herein, the term "optionally substituted alkyl" refers to monovalent straight, branched or cyclic paraffinic hydrocarbon groups that may be derived from an alkane by dropping one hydrogen from the formula. Alkyl groups preferably have from 1 to 20 carbon atoms, more preferably 1 to 10 carbon atoms, and most preferably 1 to 7 carbon atoms. This term is exemplified by groups such as methyl, ethyl, n-propyl, iso-propyl, n-butyl, iso-butyl, n-hexyl, cyclopentyl, norbornyl and the like. Such alkyl groups can optionally be substituted with from 1 to 5 substituents and preferably 1 to 3 substituents selected from the group consisting of hydroxy, acyl, optionally substituted alkyl, alkoxy, alkylthio, alkenyl, alkynyl, optionally substituted amino, acyloxy, acylamino, optionally substituted aryl, aralkyl, aryloxy, azido, carboxy, cyano, halo, nitro, heteroaryl, heteroaryloxy, trihalomethoxy, dihalomethyl, trihalomethyl, perhaloalkyl. Preferred substituents include alkyl, alkoxy, halo, carboxy, and hydroxy.

The term "lower alkyl" refers to those alkyl groups as described above having 1-6, preferably 2-4 carbon atoms.

As used herein, the term "alkoxy" refers to optionally substituted alkyl-O.

As used herein, the term "alkoxycarbonyl" refers to alkoxy-C(O).

As used herein, the term "alkylthio" refers to optionally substituted alkyl-S.

As used herein, the term "alkenyl" refers to alkenyl groups preferably having from 2 to 10 carbon atoms and more preferably 2 to 6 carbon atoms and having at least 1 and preferably from 1-2 sites of alkenyl unsaturation. Preferred alkenyl groups include ethenyl (—CH=CH$_2$), n-propenyl (—CH$_2$CH=CH$_2$), iso-propenyl (—C(CH$_3$)=CH$_2$), and the like.

Such alkenyl groups can optionally be substituted with from 1 to 5 substituents and preferably 1 to 3 substituents selected from the group consisting of hydroxy, acyl, optionally substituted alkyl, alkoxy, alkylthio, optionally substituted amino, acyloxy, acylamino, optionally substituted aryl, carboxy, cyano, halo, heteroaryl, trihalomethoxy, dihalomethyl, trihalomethyl, perhaloalkyl. Preferred substituents include alkyl, alkoxy, halo, carboxy, and hydroxy.

As used herein, the term "alkynyl" refers to alkynyl groups preferably having from 2 to 10 carbon atoms and more preferably 2 to 6 carbon atoms and having at least 1 and preferably from 1-2 sites of alkynyl unsaturation. Preferred alkynyl groups include ethynyl, propargyl, 1-butynyl, 2-butynyl, and 2-pentynyl.

Such alkynyl groups can optionally be substituted with from 1 to 5 substituents and preferably 1 to 3 substituents selected from the group consisting of hydroxy, acyl, optionally substituted alkyl, alkoxy, alkylthio, optionally substituted amino, acyloxy, acylamino, optionally substituted aryl, carboxy, cyano, halo, heteroaryl, trihalomethoxy, dihalomethyl, trihalomethyl, perhaloalkyl. Preferred substituents include alkyl, alkoxy, halo, carboxy, and hydroxy.

As used herein, the term "aralkyl" refers to an optionally substituted aryl group bonded directly though an alkyl group, such as a benzyl group.

As used herein, the term "optionally substituted amino" refers to a primary amine (—NH$_2$), which may optionally be substituted by one or two acyl, alkyl, alkyloxycarbonyl, aryl, aryloxycarbonyl, heteroaryloxycarbonyl, heterocyclyl, or sulfonyl groups. If substituted by more than one such group, the two substituents may be of the same (e.g., two alkyl groups) or different functional groups (e.g. one alkyl and one sulfonyl group). If the two groups are of the same functional type (e.g. two alkyl groups), they may be identical (e g., two methyl groups) or dissimilar (e g., one ethyl and one cyclopentyl group).

As used herein, the term "carboxy" refers to HO$_2$C—.

As used herein, the terms "halo" or "halogen" refer to fluoro, chloro, bromo, and iodo, and preferably is either fluoro or chloro.

As used herein, the term "sulfonyl" refers to an optionally substituted alkyl, aralkyl, optionally substituted aryl, or optionally substituted heteroaryl group directly bonded through an S(O)$_2$ group, such as alkyl-S(O)$_2$, aryl-S(O)$_2$, aralkyl-S(O)$_2$, and heteroaryl-S(O)$_2$, and the like.

Pharmaceutically acceptable salts of the compounds of the present invention refer to salts formed with acids, namely acid addition salts, such as of mineral acids, organic carboxylic acids and organic sulfonic acids, e.g., hydrochloric acid, maleic acid and methanesulfonic acid, respectively.

Similarly, pharmaceutically acceptable salts of the compounds of the invention refer to salts formed with bases, namely cationic salts, such as alkali and alkaline earth metal salts, e.g., sodium, lithium, potassium, calcium and magnesium, as well as ammonium salts, e.g., ammonium, trimethylammonium, diethylammonium and tris(hydroxymethyl)-methyl-ammonium salts and salts with amino acids provided an acidic group constitutes part of the structure.

Preferred are the compounds of formula (I), designated as the A group, wherein $R^1$ is an optionally substituted furan;

or a pharmaceutically acceptable salt thereof.

Preferred are the compounds in the A group, wherein $R^3$ is C(O)NH—$R^5$ in which $R^5$ is $C_1$-$C_6$ alkyl;

or a pharmaceutically acceptable salt thereof

Particular embodiments in the A group are:

(2S, 3S, 4R, 5R)-5-{6-[N'-(Furan-2-carbonyl)-hydrazino]-9H-purin-9-yl}-3,4 -dihydroxy-tetrahydrofuran-2-carboxylic acid ethylamide;

(2S, 3S, 4R, 5R)-5-{6-[N'-(5-Bromo-furan-2-carbonyl)-hydrazino]-9H-purin-9-yl}-3,4-dihydroxy-tetrahydrofuran-2-carboxylic acid ethylamide;

(2S, 3S, 4R, 5R)-3,4-Dihydroxy-5-{6-[N'-(5-methyl-furan-2-carbonyl)-hydrazino]-9H-purin-9 -yl}-tetrahydrofuran-2-carboxylic acid ethylamide; or (2S, 3S, 4R, 5R)-5-{2-Chloro-6-[N'-(furan-2-carbonyl)-hydrazino]-9H-purin-9-yl}-3,4 -dihydroxy-tetrahydrofuran-2-carboxylic acid ethylamide; or a pharmaceutically acceptable salt thereof, Preferred are also the compounds of formula (I), designated as the B group, wherein $R^1$ is an optionally substituted thiophene;

or a pharmaceutically acceptable salt thereof.

Preferred are the compounds in the B group, wherein
$R^3$ is C(O)NH—$R^5$ in which
$R^5$ is $C_1$-$C_6$ allyl:
or a pharmaceutically acceptable salt thereof.

Particular embodiments in the B group are:
(2S, 3S, 4R, 5R)-3,4-Dihydroxy-5-{6-[N'-(5-methyl-thiophene-2-carbonyl)-hydrazino]-9H-purin-9-yl}-tetrahydrofuran-2-carboxylic acid ethylamide;

(2S, 3S, 4R, 5R)-5-{2-Chloro-6-[N'-(5-methyl-thiophene-2-carbonyl)-hydrazino]-9H-purin-9 -yl}-3,4-dihydroxy-tetrahydrofuran-2-carboxylic acid ethylamide;

(2S, 3S, 4R, 5R)-5-{2-Chloro-6-[N'-(thiophene-3-carbonyl)-hydrazino]-9H-purin-9-yl}-3,4-dihydroxy-tetrahydrofuran-2-carboxylic acid ethylamide;

(2S, 3S, 4R, 5R)-5-{2-Chloro-6-[N'-(thiophene-2-carbonyl)-hydrazino]-9H-purin-9-yl}3,4-dihydroxy-tetrahydrofuran-2-carboxylic acid ethylamide;

(2S, 3S, 4R, 5R)-5-{2-Chloro-6-[N'-(3-methyl-thiophene-2-carbonyl)-hydrazino]-9H-purin-9-yl}-3,4-dihydroxy-tetrahydrofuran-2-carboxylic acid ethylamide; or (2S, 3S, 4R, 5R)-5-{2-Chloro-6-[N'-(2-thiophene-2-yl-acetyl)-hydrazino]-9H-purin-9-yl}-3,4-dihydroxy-tetrahydrofuran-2-carboxylic acid ethylamide; or a pharmaceutically acceptable salt thereof.

Preferred are the compounds of formula (I), designated as the C group, wherein
$R^1$ is an optionally substituted monocyclic aryl or heteroaryl;
or a pharmaceutically acceptable salt thereof.

Preferred are the compounds in the C group, wherein
$R^3$ is C(O)NH—$R^5$ in which
$R^5$ is $C_1$-$C_6$ alkyl;
or a pharmaceutically acceptable salt thereof.

Particular embodiments in the C group are:
(2S, 3S, 4R, 5R)-5-[6-(N'-Benzoyl-hydrazino)-9H-purin-9-yl]-3,4-dihydroxy-tetrahydrofuran-2 carboxylic acid ethylamide;

(2S, 3S, 4R, 5R)-5-{6-[N'-(4-Chloro-benzoyl)-hydrazino]-9H-purin-9-yl}-3,4-dihydroxy-tetrahydrofuran-2-carboxylic acid ethylamide;

(2S, 3S, 4R, 5R)-3,4-Dihydroxy-5-{6-[N'-(pyridine-3-carbonyl)-hydrazino]-9H-purin-9-yl}-tetrahydrofuran-2-carboxylic acid ethylamide;

(2S, 3S, 4R, 5R)-3,4-Dihydroxy-5-{6-[N'-(1-methyl-4-nitro-1H-imidazole-2-carbonyl)-hydrazino]-9H-purin-9-yl}-tetrahydrofuran-2-carboxylic acid ethylamide;

(2S, 3S, 4R, 5R)-5-[6-{N'-Benzoyl-hydrazino)-2-chloro-9H-purin-9-yl]-3,4-dihydroxy-tetrahydrofuran-2-carboxylic acid ethylamide;

(2S, 3S, 4R, 5R)-5-{2-Chloro-6-[N'-(1H-pyrrole-2-carbonyl)-hydrazino]-9H-purin-9-yl}-3,4-dihydroxy-tetrahydrofuran-2-carboxylic acid ethylamide;

(2S, 3S, 4R, 5R)-5-{2-Chloro-6-[N'-(5-methyl-isoxazole-3-carbonyl)-hydrazino]-9H-purin-9-yl}-3,4-dihydroxy-tetrahydrofuran-2-carboxylic acid ethylamide; or (2S, 3S, 4R, 5R)-5-{2-Chloro-6-[N'-(5-phenyl-isoxazole-3-carbonyl)-hydrazino]-9H-purin-9-yl}-3,4-dihydroxy-tetrahydrofuran-2-carboxylic acid ethylamide;

or a pharmaceutically acceptable salt thereof,

Compounds of formula (I) may be prepared using methods well known in the art, or using modifications thereof; or they may be prepared as described herein below. For example, compounds of formula (I) wherein $R^3$ is C(O)NH—$R^5$ may be obtained from compounds of formula (5a) as follows:

A compound of formula (5a)

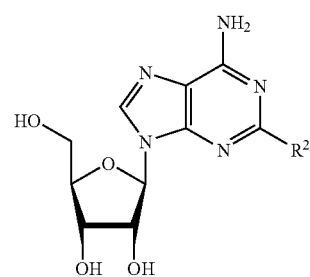

(5a)

wherein $R^2$ is H or Cl; may be converted to a compound of formula (II)

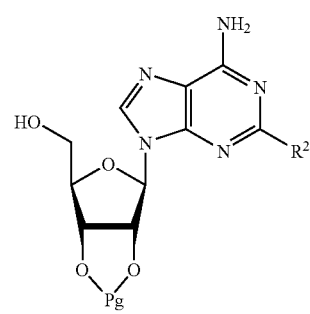

(II)

wherein $R^2$ has meaning as defined herein above; and Pg represents a suitable diol protecting group. Suitable diol protecting groups are well known in the art and include, but are not limited to, protecting groups such as isopropylidene, benzylidene and the like.

A resulting compound of formula (II) may then be treated with a suitable oxidizing agent, e.g., potassium permanganate ($KMnO_4$) in the presence of potassium hydroxide (KOH), to afford a compound of formula (III)

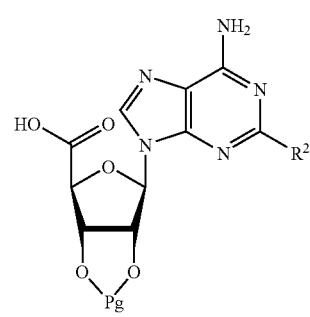

(III)

wherein $R^2$ and Pg have meaning as defined herein above.

A resulting compound of formula (III) may then be treated, e.g., with a chlorinating agent such as thionyl chloride ($SOCl_2$), followed by coupling of the intermediate acid chloride with an amine of formula (IV)

$R^5$—$NH_2$ (IV)

wherein $R^5$ is $C_1$-$C_6$ alkyl; to afford a compound of formula (V)

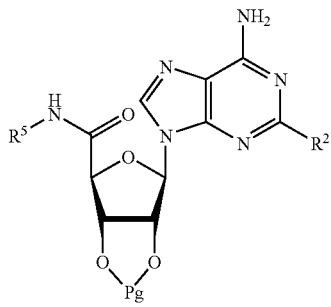

(V)

wherein $R^2$, $R^5$ and Pg have meaning as defined herein above.

A resulting compound of formula (V) may then be treated with a suitable diazotization reagent, e.g., isopentyl nitrite, in the presence of a suitable halogen source, e.g., dihalomethane such as diiodomethane, to produce a compound of formula (VI)

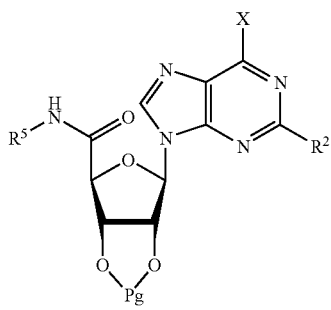

(VI)

wherein $R^2$, $R^5$ and Pg have meaning as defined herein above; and X is I, Br, Cl, or F.

A subsequent treatment of a resulting compound of formula (VI) with a hydrazide derivative of formula (VII)

$$R^1—(CH_2)_n—C(O)—NH—NH_2 \qquad (VII)$$

wherein $R^1$ is an optionally substituted aryl or heteroaryl; and n is zero or 1; then affords a compound of formula (VIII)

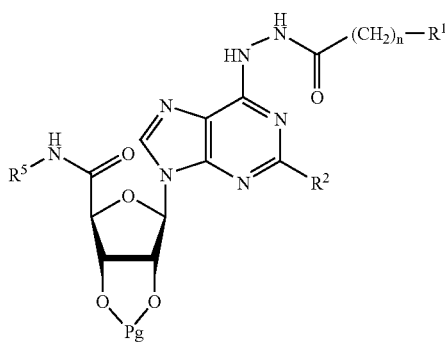

(VIII)

wherein $R^1$, n, $R^2$, $R^5$ and Pg have meaning as defined herein above.

Finally, a resulting compound of formula (VIII) may be converted to a compound of formula (I)

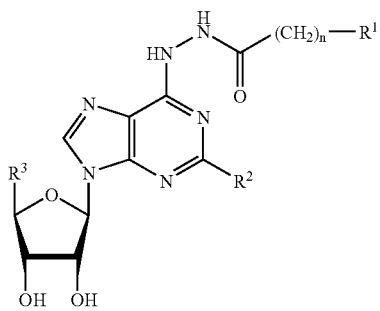

(I)

wherein $R^1$, $R^2$, $R^3$ and $R^5$ have meaning as defined herein above; by removal of the diol protecting group Pg.

In a specific embodiment of the present invention, compounds of formula (I) wherein $R^3$ is C(O)NH—$R^5$, e.g., those of formula (9b) to (26b), may be prepared as outlined in Scheme 1.

Scheme 1:

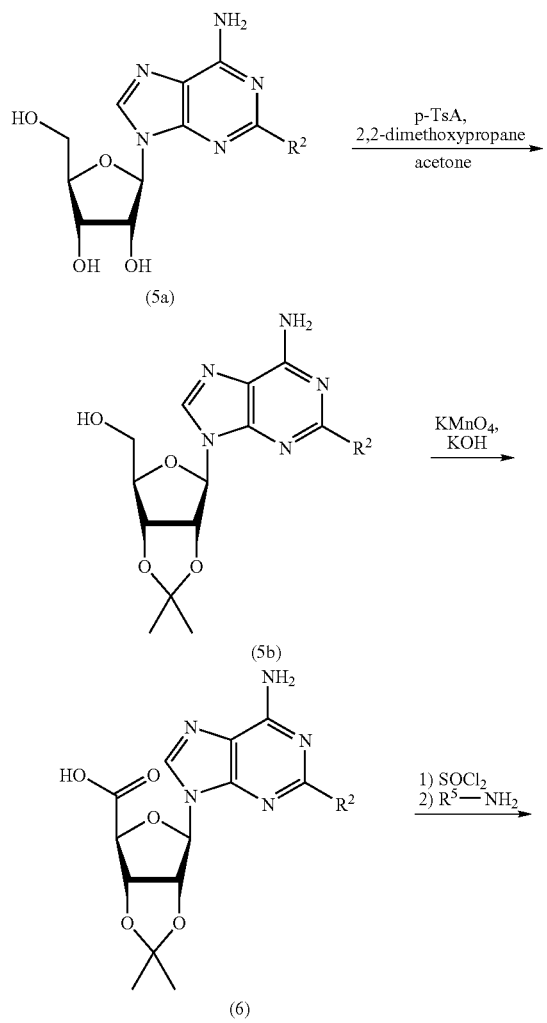

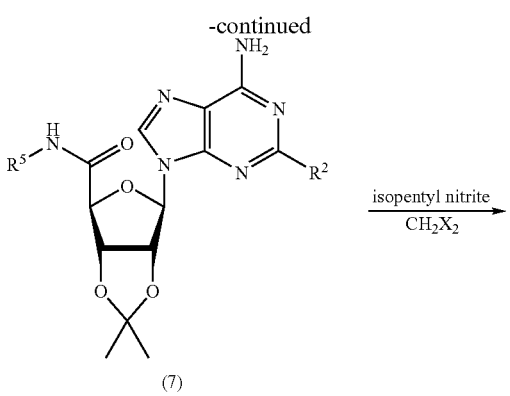

(7)

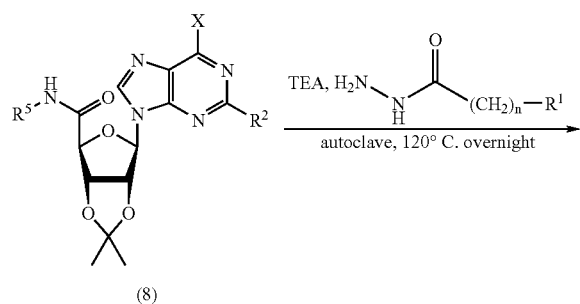

(8)

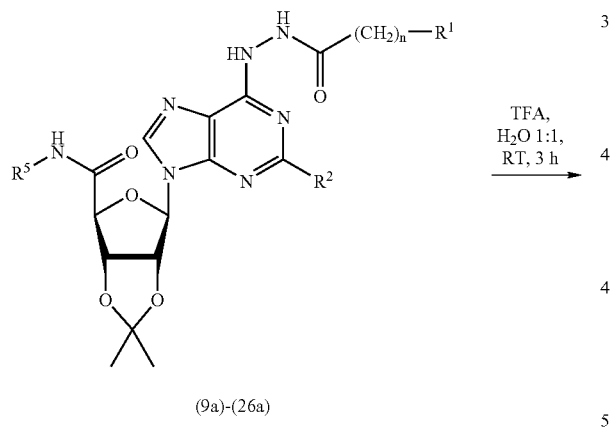

(9a)-(26a)

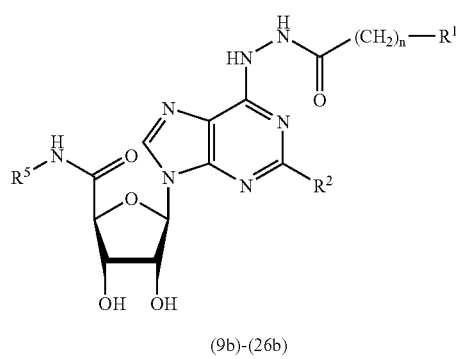

(9b)-(26b)

As illustrated in Scheme 1, compounds of formula (I) may be obtained from 2',3'-O-isopropylidene-5'-N-carboxamidoadenosine derivatives of formula (7) wherein $R^2$ and $R^5$ have meaning as described herein above, by conversion into the corresponding 6-halo, e.g., 6-iodo, derivatives of formula (8) wherein X represents halogen, e.g., iodide, by treatment with dihalomethane and isopentyl nitrite, e g, as described by Nair and Richardson in "Modification of nucleic acid bases via radical intermediates: synthesis of dihalogenated purine nucleosides", Synthesis, 1982, 670-672.

The resulting 6-halo intermediates of formula (8) wherein $R^2$, $R^5$ and X have meaning as described herein above, may then be subjected to a substitution reaction with an appropriate hydrazide reagent to afford, e.g., compounds of formula (9a)-(26a). The substitution reactions may be performed at about 100° C. in a steel bomb, for about 7-8 hours. The protected $N^6$-substituted nucleoside derivatives, e.g., those of formula (9a)-(26a) may be deprotected, e.g., by stirring for about 3 h at room temperature (RT) in a 1:1 mixture of water and trifluoroacetic acid, to give compounds of formula (I), e.g., those of formula (9b)-(26b), after purification by column chromatography, e.g., on Merck 230-400 mesh silica gel with appropriate mixtures of ethyl acetate/methanol.

Compounds of formula (I) wherein $R^1$, n and $R^2$ have meaning as defined herein above, and $R^3$ is

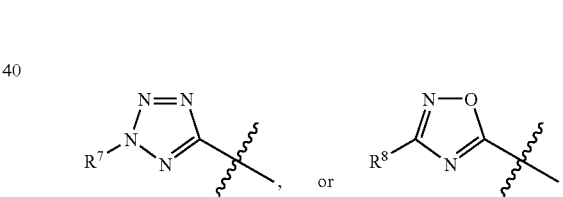

in which $R^6$, $R^7$, and $R^8$ are H or $C_1$-$C_6$ alkyl, may be prepared using methods described herein above, or modifications thereof, in combination with methods known in the art, e.g., those disclosed in U.S. Pat. No. 6,426,337 and U.S. Pat. No. 6,610,665; and International PCT Application Publications WO 99/067263, WO 99/067266 and WO 99/067264. Likewise, compound of formula (I) wherein $R^1$, n and $R^2$ have meaning as defined herein above, and $R^3$ is $CH_2OR^4$ in which $R^4$ is H or $C_1$-$C_6$ alkyl provided $R^4$ is not H when n is zero and $R^1$ is unsubstituted phenyl, may be prepared using methods described herein above, or modifications thereof; in combination with methods known in the art, e.g., those disclosed in U.S. Pat. No. 6,326,359.

The physico-chemical parameters for compounds of formula (9b)-(26b) are shown in Table 1 (melting points are determined on a Buchi-Tottoli instrument and are uncorrected; and elemental analyses are within ±0.4% of the theoretical values for C, H and N).

TABLE 1

(9b)-(26b)

[Structure: purine nucleoside with HN-NH-C(O)-(CH₂)ₙ-R¹ at 6-position, R² at 2-position, ribose with R³ and OH, OH]

| Comp | R¹ | n | R² | R³ | R⁵ | mp (° C.) | MW | Formula |
|---|---|---|---|---|---|---|---|---|
| 9b | Phenyl | 0 | H | C(O)NH—R⁵ | Et | 174-175 | 427.16 | $C_{19}H_{21}N_7O_5$ |
| 10b | 4-Chlorophenyl | 0 | H | C(O)NH—R⁵ | Et | 188-189 | 461.86 | $C_{19}H_{20}ClN_7O_5$ |
| 11b | 3-Pyridyl | 0 | H | C(O)NH—R⁵ | Et | 170 | 428.40 | $C_{18}H_{20}N_8O_5$ |
| 12b | 2-Furyl | 0 | H | C(O)NH—R⁵ | Et | 233-234 | 417.38 | $C_{17}H_{19}N_7O_6$ |
| 13b | 5-Bromo-furan-2-yl | 0 | H | C(O)NH—R⁵ | Et | 171 | 496.27 | $C_{17}H_{18}BrN_7O_6$ |
| 14b | 5-Methyl-furan-2-yl | 0 | H | C(O)NH—R⁵ | Et | 154-155 | 431.4 | $C_{18}H_{21}N_7O_6$ |
| 15b | 1-Methyl-4-nitro-1H-imidazol-2-yl | 0 | H | C(O)NH—R⁵ | Et | 169-170 | 476.40 | $C_{17}H_{20}N_{10}O_7$ |
| 16b | 5-Methyl-thiophen-2-yl | 0 | H | C(O)NH—R⁵ | Et | 153-154 | 447.47 | $C_{18}H_{21}N_7O_5S$ |
| 17b | Phenyl | 0 | Cl | C(O)NH—R⁵ | Et | 253-254 | 461.86 | $C_{19}H_{20}ClN_7O_5$ |
| 18b | 2-Furyl | 0 | Cl | C(O)NH—R⁵ | Et | 269-270 | 451.82 | $C_{17}H_{18}ClN_7O_6$ |
| 19b | 5-Methyl-thiophen-2-y | 0 | Cl | C(O)NH—R⁵ | Et | 156 | 481.91 | $C_{18}H_{20}ClN_7O_5S$ |
| 20b | (Thiophen-2-yl)- | 1 | Cl | C(O)NH—R⁵ | Et | 153-154 | 481.91 | $C_{18}H_{20}ClN_7O_5S$ |
| 21b | Thiophen-3-yl | 0 | Cl | C(O)NH—R⁵ | Et | 249-250 | 467.89 | $C_{17}H_{18}ClN_7O_5S$ |
| 22b | Thiophen-2-yl | 0 | Cl | C(O)NH—R⁵ | Et | 189-190 | 467.89 | $C_{17}H_{18}ClN_7O_5S$ |
| 23b | 3-Methyl-thiophen 2-yl | 0 | Cl | C(O)NH—R⁵ | Et | 160-161 | 481.91 | $C_{18}H_{20}ClN_7O_5S$ |
| 24b | 1H-Pyrrol-2-yl | 0 | Cl | C(O)NH—R⁵ | Et | 230-231 | 450.84 | $C_{17}H_{19}ClN_8O_5$ |
| 25b | 5-Methyl-isoxazol-3-yl | 0 | Cl | C(O)NH—R⁵ | Et | 182-183 | 466.11 | $C_{17}H_{19}ClN_8O_6$ |
| 26b | 5-Phenyl-isoxazol-3-yl | 0 | Cl | C(O)NH—R⁵ | Et | 169-170 | 528.91 | $C_{22}H_{21}ClN_8O_6$ |

The processes described herein above may be conducted under inert atmosphere, preferably under nitrogen atmosphere. The reaction progress and product mixtures may be monitored by thin-layer chromatography (TLC) on silica gel (e.g., pie-coated $F_{254}$ Merck plates) and visualized, e.g., with aqueous potassium permanganate in a methanolic solution of $H_2SO_4$.

In starting compounds and intermediates which are converted to the compounds of the present invention in a manner described herein, functional groups present, such as amino, thiol, carboxyl and hydroxyl groups, are optionally protected by conventional protecting groups that are common in preparative organic chemistry. Protected amino, thiol, carboxyl and hydroxyl groups are those that can be converted under mild conditions into free amino thiol carboxyl and hydroxyl groups without the molecular framework being destroyed or other undesired side reactions taking place.

The purpose of introducing protecting groups is to protect the functional groups from undesired reactions with reaction components under the conditions used for carrying out a desired chemical transformation The need and choice of protecting groups for a particular reaction is known to those skilled in the art and depends on the nature of the functional group to be protected (hydroxyl group, amino group, etc.), the structure and stability of the molecule of which the substituent is a part and the reaction conditions.

Well-known protecting groups that meet these conditions and their introduction and removal are described, e.g., in McOmie, "Protective Groups in Organic Chemistry", Plenum Press, London, N.Y. (1973); and Greene and Wuts, "Protective Groups in Organic Synthesis", John Wiley and Sons, Inc., NY (1999).

The above-mentioned reactions are carried out according to standard methods, in the presence or absence of diluent, preferably, such as are inert to the reagents and are solvents thereof, of catalysts, condensing or said other agents, respectively and/or inert atmospheres, at low temperatures, RT or elevated temperatures, preferably at or near the boiling point of the solvents used, and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the reaction components are used in the form of their salts.

Compounds of the invention and intermediates can also be converted into each other according to methods generally known per se.

The present invention also relates to any novel starting materials, intermediates and processes for their manufacture.

In a further aspect of the present invention, compounds of formula (I) may be labeled with radioactive isotopes, including, but not limited to, tritium ($^3H$), carbon ($^{14}C$), iodine ($^{125}I$), phosphorus ($^{31}P$, $^{32}P$, $^{33}P$), and sulfur ($^{35}S$). The compounds may also be labeled in other ways, e.g., fluorescently or with PET (Positron Emission Tomography) or SPECT (Single Photon Emission Tomography) labels. For example, the 2 or 8 position on the purine moiety may be labeled with tritium. A heteroaryl ring at the R¹ position in compounds of formula (I) may also be labeled in any suitable position by any of the methods described herein.

Also known is the use of stable isotopes, such as deuterium ($^2H$) and $^{13}C$ that are detected by magnetic resonance imaging or mass spectrometry. The compounds of this invention may be labeled or derivatized, e.g., for kinetic binding experiments, for further elucidating metabolic pathways and enzymatic mechanisms, or for characterization by methods known in the art of analytical chemistry.

As used herein, the term "labeled" includes the use of any of the methods described.

The present invention also encompasses the use of the disclosed compounds in screening assays to determine the effectiveness of other compounds for binding to the $A_{2B}$ adenosine receptor through competitive inhibition as determined by various binding assays. Such a screening assay would make use of a labeled form of one of the compounds, preferably tritiated, and would be preferably formed from 8-tritiated adenosine or 8-tritiated $N^6$-carboxamido derivatives of adenosine-5'-N-ethyluronamide (NECA) or 2,8-ditritiated compounds. Such screening assays are described in Jacobson and Van Rhee, "Purinergic approaches to experimental therapy," Jacobson and Jarvis, ed., Wiley, N.Y., 1997, pp. 101-128; Mathot et al., Brit J. Pharmacol., 116: 1957-1964 (1995); van der Wenden et al., J. Med. Chem., 38: 4000-4006 (1995); and van Calenbergh, J. Med Chem., 40: 3765-3772 (1997).

Likewise, the present invention provides a method for the induction of pharmacological stress to facilitate coronary imaging of areas of ischemia in a mammal comprising administering to the mammal an effective amount of a compound of formula (I).

The compounds of the present invention can be administered via any medically acceptable means. Suitable means of administration include oral, rectal, topical or parenteral (including subcutaneous, intramuscular and intravenous) administration, although oral or parenteral administration are preferred.

The term "therapeutically effective amount" as used herein refers to an amount of a drug or a therapeutic agent that will elicit the desired biological or medical response of a tissue, system or an animal (including man) that is being sought by a researcher or clinician.

The amount of the compound required to be therapeutically effective as an agonist of an adenosine receptor will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. However, a suitable effective dose is in the range of about 0.1 μg/kg to about 10 mg/kg body weight per day, preferably in the range of about 0.01 mg/kg to about 3 mg/kg per day, The total daily dose may be given as a single dose, multiple doses, e.g., two to six times per day, or by intravenous infusion for a selected duration. Dosages above or below the range cited above are within the scope of the present invention and may be administered to the individual patient if desired and necessary. For example, for a 75 kg mammal, a dose range would be about 7.5 μg to about 750 mg per day, and a typical dose would be about 150 mg per day. If discrete multiple doses are indicated, treatment might typically be 50 mg of a compound given 3 times per day.

The compounds described above are preferably administered in a formulation including an active compound, i.e., a compound of formula (I), or a pharmaceutically acceptable salt thereof, together with an acceptable carrier for the mode of administration. Suitable pharmaceutically acceptable carriers are known to those of skill in the art.

Accordingly, the present invention provides pharmaceutical compositions comprising a therapeutically effective amount of a compound of the invention as defined above, either alone or in a combination with another active ingredient, such as anti-inflammatories, anti-diarrheal, and anti-hypertensives, each at an effective therapeutic dose as reported in the art.

When a therapeutically effective amount of a compound of the invention, as defined above, is combined with a therapeutically effective dose of an anti-inflammatory agent, the anti-inflammatory agent may include, but not be limited to, salicylates, non-selective COX inhibitors, and selective COX-2 inhibitors.

When a therapeutically effective amount of a compound of the invention, as defined above, is combined with a therapeutically effective dose of an anti-diarrheal agent, the anti-diarrheal agent may include, but not be limited to, antimotility agents, narcotics, and anti-secretory agents.

When a therapeutically effective amount of a compound of the invention, as defined above, is combined with a therapeutically effective dose of an anti-hypertensive, the anti-hypertensive may include, but not be limited to, loop diuretics, angiotensin-converting enzyme inhibitors, inhibitors of the Na—K-ATPase membrane pump, neutral endopeptidase inhibitors, ACE/NEP inhibitors, angiotensin II receptor antagonists, β-adrenergic receptor blockers, inotropic agents, calcium channel blockers, aldosterone receptor antagonists, aldosterone synthase inhibitors, or diuretics.

A compound of the present invention may be administered either simultaneously, before, or after the other active ingredient, either separately by the same or a different route of administration or together in the same pharmaceutical formulation. The carrier must be pharmaceutically acceptable in the sense of being compatible with all ingredients of the formulation and not deleterious to the recipient thereof.

The formulations can include carriers suitable for oral, rectal, topical or parenteral (including subcutaneous, intramuscular and intravenous) administration. Preferred carriers are those suitable for oral or parenteral administration.

Formulations suitable for parenteral administration conveniently include sterile aqueous preparation of the active compound which is preferably isotonic with the blood of the recipient. Thus, such formulations may conveniently contain distilled water, 5% dextrose in distilled water or saline. Useful formulations also include concentrated solutions or solids containing the compound of formula (I) which upon dilution with an appropriate solvent give a solution suitable for parental administration above.

For enteral administration, the compound can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

The compounds may also be administered locally by topical application of a solution, ointment, cream, gel, lotion or polymeric material (for example, a Pluronic™, BASF), which may be prepared by conventional methods known in the art of pharmacy. In addition to the solution, ointment, cream, gel, lotion or polymeric base and the active ingredient, such topical formulations may also contain preservatives, perfumes, and additional active pharmaceutical agents.

Formulations for rectal administration may be presented as a suppository with a conventional carrier, e.g., cocoa butter or Witepsol S55 (trademark of Dynamite Nobel Chemical, Germany), for a suppository base.

Alternatively, the compound may be administered in liposomes or microspheres (or microparticles). Methods for preparing liposomes and microspheres for administration to a patient are well known to those of skill in the art, e.g., as described in U.S. Pat. No. 4,789,734 for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," Drug Carriers in Biolopy and Medicine, pp. 287-341 (Academic Press, 1979). Microspheres formed of polymers or proteins are well known to those skilled in the art, and can be tailored for passage through the gastrointestinal tract directly into the blood stream. For example, a drug substance can be incorporated to microspheres, or composite of microspheres, and implanted for slow release over a period of time ranging from days to months as described in U.S. Pat. No. 4,906,474, U.S. Pat. No. 4,925,673 and U.S. Pat. No. 3,625,214.

Preferred microparticles are those prepared from biodegradable polymers, such as polyglycolide, polylactide and copolymers thereof. Those of skill in the art can readily determine an appropriate carrier system depending on various factors, including the desired rate of dug release and the desired dosage.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into desired unit dosage form.

In addition to the aforementioned ingredients, the formulations may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

The above-cited properties are demonstrable in vitro and in vivo tests using advantageously mammals, e.g., mice, rats, dogs, monkeys or isolated organs, tissues and preparations thereof. Said compounds can be applied in vitro in the form of solutions, e.g., preferably aqueous solutions, and in vivo either enter ally, parenterally, advantageously intravenously, e.g., as a suspension or in aqueous solution. The dosage in vitro may range between about $10^{-2}$ molar and $10^{-9}$ molar concentrations. A therapeutically effective amount in vivo may range depending on the species and the route of administration, between about 0.01 µg/kg and 1000 mg/kg, preferably between about 0.1 mg/kg and 10 mg/kg, more preferably between about 0.01 mg/kg and 3 mg/kg.

The activity of compounds according to the invention may be assessed using methods well-described in the art, e.g., as described herein below:

Competition binding experiments are performed as described by Varani et al. in "[$^3$H]MRE 3008F20: a novel antagonist radioligand for the pharmacological and biochemical characterization of human $A_3$ adenosine receptors", Mol. Pharmacol 2000, 57, 968-975. The affinity of the synthesized compounds to bind to the $hA_1$, $hA_{2A}$ and $hA_3$ receptors expressed in CHO cells, may be evaluated using [$^3$H]-CHA, [$^3$H]-CGS 21680 and [$^{125}$I]-ABMECA as radioligands, respectively.

The effects of the tested compounds may be evaluated in functional assays measuring the stimulatory capability of the ligands to increase cAMP levels in $hA_{2B}$ receptors expressed in CHO cells. This may done as described by Pastorin et al. in "Pyrazolo[4,3-e]-1,2,4-triazolo[1,5-c]pyrimidine derivatives as adenosine receptor antagonists. Influence of the $N^5$-substituent on the affinity at the human $A_3$ and $A_{2B}$ adenosine receptor subtypes: a molecular modeling investigation" J. Med. Chem. 2003, 46, 4287-4296.

The expression of the human $A_1$, $A_{2A}$, $A_{2B}$ and $A_3$ receptors in CHO cells has been previously described (Klotz et al. "Comparative pharmacology of human adenosine receptor subtypes—characterization of stably transfected receptors in CHO cells", Naunyn Schmiedeberg's Arch Pharmacol., 1998, 357:1-9). The cells are grown adherently and maintained in Dulbecco's Modified Eagles Medium with nutrient mixture F12 (DMEM/F12) without nucleosides, containing 10% fetal calf serum, penicillin (100 U/mL), streptomycin (100 µg/mL), L-glutamine (2 mM) and Geneticin (G418, 0.2 mg/mL) at 37° C. in 5% $CO_2$/95% air. Cells are split 2 or 3 times weekly at a ratio between 1:5 and 1:20. For membrane preparation the culture medium is removed and the cells are washed with PBS and scraped off T75 flasks in ice-cold hypotonic buffer (5 mM Tris HCl, 2 mM EDTA, pH 7.4). The cell suspension is homogenized and centrifuged for 30 min at 100,000×g. The membrane pellet is re-suspended in 50 mM Tris HCl buffer pH 7.4 and incubated with 2 UI/mL of adenosine deaminase for 30 min at 37° C. Then the suspension is frozen at −80° C. and the protein concentration is determined according to a Bio-Rad method (Bradford M. M. "A rapid and sensitive method for the quantitation of microgram quantities of protein utilizing the principle of protein-dye binding", Anal Biochem. 1976, 7, 248-54) with bovine albumin as a standard reference.

Binding of 1 nM [$^3$H]—CHA to $hA_1$CHO cells (50 µg of protein/assay) is performed using 50 mM Tris HCl buffer pH 7.4 and at least 6-8 different concentrations of agonists studied for an incubation time of 150 min at 25° C. (Borea et al. "Binding thermodynamics at $A_1$ and $A_{2A}$ adenosine receptors", Life Sciences 1996, 59:1373-1388). Non-specific binding is determined in the presence of 10 µM of CHA and is about 20% of the total binding. Inhibition binding experiments of [$^3$H]-CGS 21680 to hA$_{2A}$ CHO cells (100 μg of protein/assay) are performed using 50 mM Tris HCl buffer, 10 mM MgCl$_2$ pH 7.4 and at least 6-8 different concentrations of agonists studied for an incubation time of 180 min at 25° C. (Borea et al. "Binding thermodynamics of adenosine A$_{2A}$ receptor ligands", Biochem. Pharmacol. 1995, 49:461-469). Non-specific binding is determined in the presence of 10 μM of CGS 21680 and is about 25% of the total binding Separation of bound from free radioligand is performed by rapid filtration through Whatman GF/B filters which are washed three times with ice-cold buffer. Filter bound radioactivity is measured by scintillation spectrometry after addition of 5 mL of Aquassure.

For cell preparation CHO cells transfected with human A$_{2B}$ or A$_3$ receptors are washed with phosphate-buffered saline and diluted trypsin, and centrifuged for 10 min at 200 g. The pellet containing the CHO cells (1×10$^6$ cells/assay) is suspended in the incubation mixture (mM): NaCl 15, KCl 0.27, NaH$_2$PO$_4$ 0,037, 2 IU/mL adenosine deaminase and 4-(3-butoxy-4-methoxy-benzyl)-2-imidazolidone (Ro 20-1724) as phosphodiesterase inhibitor and preincubated for 10 min in a water bath at 37° C. After the preincubation time at 37° C., the examined ligands (1 nM-10 μM) are added to the mixture and incubated for a further 5 min. The reaction is terminated by the addition of cold 6% trichloroacetic acid (TCA). The TCA suspension is centrifuged at 2000 g for 10 min at 4° C. and the supernatant is extracted four times with water saturated diethyl ether. The final aqueous solution is tested for cyclic AMP levels by a competition protein binding assay (Varani et al. "[$^3$H]—SCH 58261 labelling of functional A$_{2A}$ adenosine receptors in human neutrophil membranes", Br. J., Pharmacol., 1998, 123:1723-1731). Samples of cyclic AMP standard (0-10 pmoles) are added to each test tube containing the incubation buffer (trizma base 0.1 mM, aminophylline 8.0 mM, 2-mercaptoethanol 6.0 mM, pH 7.4) and [$^3$H]cyclic AMP in total volume of 0.5 mL. The binding protein previously incubated at 4° C. for 150 min, and after the addition of charcoal is centrifuged at 2000 g for 10 min. The clear supernatant is counted in a Beckman scintillation counter.

Inhibitory binding constant, K$_i$, values are calculated from those of IC$_{50}$ according to Cheng & Prusoff equation (Cheng Y. and Prusoff W. H. "Relationship between the inhibition constant (K$_i$) and the concentration of inhibitor which causes 50 per cent inhibition (I$_{50}$) of an enzymatic reaction", Biochem. Pharmacol. 1973, 1:3099-108):

$$K_i = IC_{50}/(1+[C^*]/K_D^*),$$

wherein [C*] is the concentration of the radioligand and K$_D$* its dissociation constant. A weighted non-linear least-squares curve fitting program LIGAND (Munson P. J., Rodbard D. "Ligand: a versatile computerized approach for characterization of ligand-binding systems" Anal. Biochem. 1980, 107: 220-39) is used for computer analysis of inhibition binding experiments. The EC$_{50}$ and IC$_{50}$ values obtained in cyclic AMP assay are calculated by non linear regression analysis using the equation for a sigmoid concentration-response curve (GraphPad Prism, San Diego, Calif., U.S.A.). All experimental data are expressed as the mean±standard error of the mean (s.e. mean) of three or four independent experiments performed in duplicate.

TABLE 2

Binding and Functional Data of the Synthesized NECA Derivatives 9b-26b

| Compd. | [$^3$H]CHA binding hA$_1$ CHO cells Ki(nM) | [$^3$H]CGS21680 binding hA$_{2A}$ CHO cells Ki(nM) | cAMP assay hA$_{2B}$ CHO cells EC$_{50}$ (nM) | cAMP assay hA$_3$ CHO cells IC$_{50}$ (nM) | Selectivity hA$_1$/hA$_{2B}$ | hA$_{2A}$/hA$_{2B}$ | hA$_3$/hA$_{2B}$ |
|---|---|---|---|---|---|---|---|
| 1 (NECA) | 18.3 ± 2.5 | 12.5 ± 2.8 | 160 ± 20 | 34.6 ± 3.3 | 0.11 | 0.08 | 0.21 |
| 9b | >1000 | >1000 | >1000 | >1000 | — | — | — |
| 10b | >1000 | >1000 | >1000 | >1000 | — | — | — |
| 11b | >1000 | >1000 | >1000 | >1000 | — | — | — |
| 12b | >1000 | >1000 | 82 ± 10 | >1000 | >12.19 | >12.19 | >12.19 |
| 13b | — | — | — | — | — | — | — |
| 14b | 700 ± 25 | 1300 ± 50 | 227 ± 18 | >1000 | 3.08 | 5.73 | >4.40 |
| 15b | >1000 | >1000 | >1000 | >1000 | — | — | — |
| 16b | >1000 | >1000 | 273 ± 12 | >1000 | >3.66 | >3.66 | >3.66 |
| 17b | >1000 | >1000 | >1000 | >1000 | — | — | — |
| 18b | >1000 | >1000 | 210 ± 13 | >1000 | >4.76 | >4.76 | >4.76 |
| 19b | >1000 | >1000 | 175 ± 20 | >1000 | >5.71 | >5.71 | >5.71 |
| 20b | 62 ± 4 | 633 ± 60 | 603 ± 31 | 67 ± 4 | 0.10 | 1.05 | 0.11 |
| 21b | 933 ± 76 | >1000 | 450 ± 29 | >1000 | 2.07 | >2.22 | >2.22 |
| 22b | 737 ± 76 | >1000 | 200 ± 20 | >1000 | 3.68 | >5.00 | >5.00 |
| 23b | >1000 | >1000 | 340 ± 35 | >1000 | >2.94 | >2.94 | >2.94 |
| 24b | 610 ± 32 | >1000 | 359 ± 36 | >1000 | 1.70 | >2.78 | >2.78 |
| 25b | >1000 | >1000 | >1000 | >1000 | — | — | — |
| 26b | >1000 | >1000 | >1000 | >1000 | — | — | — |

The Examples disclosed herein are intended to illustrate the invention and are not to be construed as being limitations thereon. If not mentioned otherwise, all evaporations are performed under reduced pressure, preferably between about 10 mmHg and 100 mmHg. The structure of final products, intermediates and starting materials is confirmed by standard analytical methods, e.g., microanalysis, melting point (mp) and spectroscopic characteristics, e.g., MS, IR and NMR. Abbreviations used herein are those conventional in the art.

EXAMPLE 1

2',3'-O-Isopropylidene-6-iodo-NECA (Compound 8)

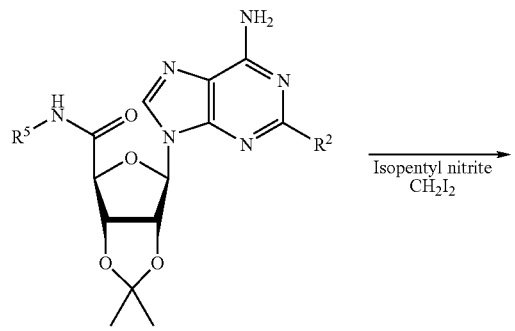

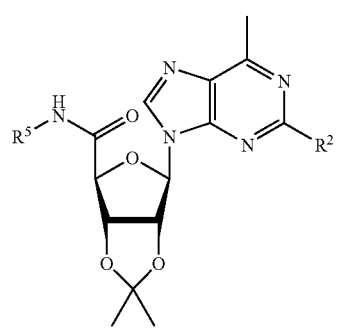

A mixture of 2',3'-isopropylidene-NECA (0.2 g, 0.57 mmol) and isopentyl nitrite (1.65 mL) in $CH_2I_2$ (4.30 mL) is stirred at 85° C. for 1 hour then the excess reagent is removed under vacuum to obtain a residue which is dissolved in $CH_2Cl_2$. The organic phase is washed with water, dried with $Na_2SO_4$, and the solvent is removed to give a dark oil that is washed with petroleum ether. The product is isolated from the crude oil by column chromatography and purified by crystallization:

(3aS, 4S, 6R, 6aR)-6-(6-Iodo-9H-purin-9-yl)-2,2-dimethyl-tetrahydrofuro[3,4-d][1,3] dioxole-4-carboxylic acid ethylamide (Compound 8, $R^2$=H; $R^5$=Et). The product is purified by column chromatography with silica gel eluting with a mixture of $CH_2Cl_2/CH_3OH$ 9.8:9.2 and crystallizing with a mixture of $CH_2Cl_2$/Light petroleum 1:2. Yellow solid; 60% yield, mp 79-80° C.; $^1$H-NMR (200 MHz, DMSO-$d_6$): δ (ppm) 0.49 (t, 3H, J=7.2), 1.32 (s, 3H), 1.52 (s, 3H), 2.70 (m, 2H), 4.50-4.60 (m, 1H), 5.43 (s, 2H), 6.42 (s, 1H), 7.47 (bt, 1H), 8.43 (s, 1H), 8.47 (s, 1H).

(3aS, 4S, 6R, 6aR)-6-(2-Chloro-6-iodo-9H-purin-9-yl)-2,2-dimethyl-tetrahydrofuro[3,4-d][1,3]dioxole-4-carboxylic acid ethylamide (Compound 8, $R^2$=Cl; $R^5$=Et). The product is purified by column chromatography with silica gel eluting with a mixture of EtOAc/Light petroleum 3:7 and crystallizing with a mixture of EtOAc/Et$_2$O/Light Petroleum 1:1:1 White solid; 70% yield; mp 95° C.; $^1$H-NMR (200 MHz, DMSO-$d_6$): δ (ppm) 0.55 (t, 3H, J=7.2), 1.35 (s, 3H), 1.53 (s, 3H), 2.80 (m, 2H), 4.61 (s, 1H), 5.43 (m, 2H), 6.42 (s, 1H), 7.58 (bt, 1H), 8.77 (s, 1H).

EXAMPLE 2

2',3'-O-Isopropylidene-6-substituted adenosine-5'-N-ethyluronamides (Compounds 9a-26a)

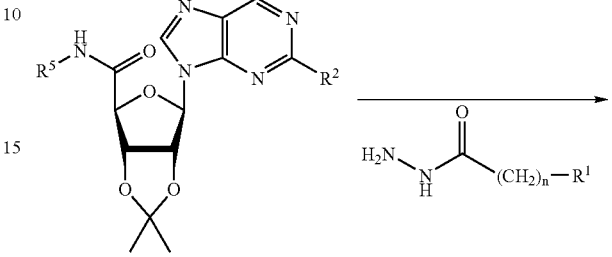

A mixture of the iodo-derivative, $NH_2NHC(O)Ar$ (1.5 eq), and triethylamine (1.5 eq) in EtOH is heated in a steel bomb for 24 hours at 120-130° C. The solvent is evaporated and the residue purified by column chromatography (different mixtures of ethyl acetate and methanol):

(3aS, 4S, 6R, 6aR)-6-[6-(N'-Benzoyl-hydrazino)-9H-purin-9-yl]-2,2-dimethyl-tetrahydrofuro[3,4-d]-1,3-dioxole-4-carboxylic acid ethylamide (Compound 9a). The product is purified by crystallization with a mixture of Et$_2$O/Petroleum ether 1:2. Pale yellow solid; mp 124-125° C.; $^1$H-NMR (200 MHz, DMSO-$d_6$): δ (ppm) 0.64 (t, 3H, J=7.2), 1.32 (s, 3H3, 1.52 (s, 3H), 2.83 (bm, 2H), 4.53 (bs, 1H), 5.38 (bs, 2H), 6.35 (bs, 1H), 7.20 (bm, 1H), 7.49-7.57 (m, 3H), 7.90-7.95 (m, 2H) 8.21 (s, 1H), 8.40 (bs, 1H), 10.00-11.00 (bs, 2H)

(3aS, 4S, 6R, 6aR)-6-(6-[N'-4-Chloro-benzoyl)-hydrazino]-9H-purin-9-yl)-2,2-dimethyl-tetrahydrofuro[3,4-d] [1,31 dioxole-4-carboxylic acid ethylamide (Compound 10a). The product is purified by column chromatography on silica gel eluting with a mixture of EtOAc/Petroleum ether 1:1. White solid; mp 116-117° C.; $^1$H-NMR (200 MHz, DMSO-$d_6$): δ (ppm) 0.80 (t, 3H, J=7.2), 1.32 (s, 3H), 1.54 (s, 3H), 3.04 (m, 2H), 4.57 (s, 1H), 5.30 (s, 2H), 6.17 (s, 1H), 7.18 (bt, 1H), 7.38 (d, 2H, J=8), 7.92 (d, 2H, J=8), 8.01 (s, 1H), 8.26 (s, 1H), 9.30 (bs, 1H), 10.56 (bs, 1H).

(3aS, 4S, 6R, 6aR)-2,2-Dimethyl-6-{6-[N'-(pyridine-3-carbonyl)-hydrazino]-9H-purin-9-yl}-tetrahydrofuro[3,4-cd][1,3]dioxole-4-carboxylic acid ethylamide (Compound 11a). The product is purified by column chromatography on silica gel eluting with a mixture of EtOAc/CH$_3$OH 9.5:0.5. White solid; mp 144-145° C.; $^1$H-NMR (200 MHz, DMSO-$d_6$): δ (ppm) 0.63 (t, 3H, J=7.2), 1.33 (s, 3H), 1.53 (s, 3H), 2.81 (bm, 2H), 4.55 (s, 1H), 5.40 (s, 2H), 6.37 (s, 1H), 7.57 (bs, 2H), 8.25 (bm, 3H), 8.77 (s, 1H), 9.09 (s, 1H), 9.95 (bs, 1H), 10.85 (bs, 1H).

(3aS, 4S, 6R, 6aR)-6-{6-[N'-(Furan-2-carbonyl)-hydrazino]-9H-purin-9-yl}-2,2-dimethyl-tetrahydrofuro [3,4-d][1,3]dioxole-4-carboxylic acid ethylamide (Compound 12a) The product is purified by column chromatography on silica gel eluting with EtOAc. White solid; mp 128-129° C.; $^1$H-NMR (200 MHz, DMSO-d$_6$): δ (ppm) 0.64 (t, 3H, J=7.2), 1.34 (s, 3H), 1.54 (s, 3H), 2.76 (m, 2H), 4.55 (s, 1H), 5.40 (s, 2H), 6.37 (s, 1H), 6.67 (m, 1H), 7.25 (d, 1H, J=3.3), 7.58 (bt, 1H), 7.92 (s, 1H), 8.23 (s, 1H), 8.38 (bs, 1H), 9.85 (bs, 1H), 10.50 (bs, 1H).

(3aS, 4S, 6R, 6aR)-6-{6-[N'-(5-Bromo-furan-2-carbonyl)-hydrazino]-9H-purin-9-yl}-2,2-dimethyl-tetrahydrofuro[3,4-d][1,3]dioxole-4-carboxylic acid ethylamide (Compound 13a). The product is purified by column chromatography on silica gel eluting with EtOAc. Pale yellow solid; mp 118-120° C.; $^1$H-NMR (200 MHz, DMSO-d$_6$): δ (ppm) 0.64 (t, 3H, J=7.2), 1.34 (s, 3H), 1.54 (s, 3H), 2.79 (bm, 2H), 4.55 (s, 1H), 5.40 (bs, 2H), 6.37 (s, 1H), 6.81 (d, 1H, J=3.8), 7.28 (d, 1H, J=3.6), 7.56 (bt, 1H), 8.23 (s, 1H), 8.39 (bs, 1H), 9.90 (bs, 1H), 10.60 (bs, 1H).

(3aS, 4S, 6R, 6aR)-2,2-Dimethyl-6-{6-[N'-(5-methyl-furan-2-carbonyl)-hydrazino]-9H-purin-9-yl}-tetrahydrofuro[3,4-d][1,3]dioxole-4-carboxylic acid ethylamide (Compound 14a). The product is purified by column chromatography on silica gel eluting with EtOAc. Pale yellow solid; mp 126-127° C.; $^1$H-NMR (400 MHz, DMSO-d$_6$): δ (ppm) 0.65 (t, 3H, J=7.2), 1.34 (s, 3H), 1.53 (s, 3H), 2.36 (s, 3H), 2.80 (bm, 2H), 4.55 (s, 1H), 5.40 (bs, 2H), 6.29 (m, 1H), 6.40 (bs, 1H), 7.14 (m, 1H), 7.57 (bt, 1H), 8.22 (s, 1H), 8.40 (bs, 1H), 9.80 (bs, 1H), 10.28 (bs, 1H).

(3aS, 4S, 6R, 6aR)-2,2-Dimethyl-6-{6-[N'-(1-methyl-4-nitro-1H-imidazole-2-carbonyl)-hydrazino]-9H-purin-9-yl}-tetrahydrofuro[3,4-d][1,3]diozole-4-carboxylic acid ethylamide (Compound 15a). The product is purified by column chromatography on silica gel eluting with a mixture of EtOAc/CH$_3$OH 9.5:0.5 White solid; mp 155-156° C.; $^1$H-NMR (200 MHz, DMSO-d$_6$): δ (ppm) 0.65 (t, 3H, J=7.2), 1.33 (s, 3H), 1.54 (s, 3H), 2.78 (m, 2H), 3.45 (s, 3H), 4.55 (s, 1H), 5.40 (s, 2H), 6.37 (s, 1H), 7.51 (bt, 1H), 8.24 (s, 1H), 8.39 (s, 1H), 8.60 (s, 1H), 9.80 (bs, 1H), 10.50 (bs, 1H).

(3aS, 4S, 6R, 6aR)-2,2-Dimethyl-6-{6-[N'-(5-methyl-thiophene-2-carbonyl)-hydrazino]-9H-purin-9-yl}-tetrahydrofuro[3,4-d][1,3]dioxole-4-carboxylic acid ethylamide (Compound 16a). The product is purified by column chromatography on silica gel eluting with a mixture of EtOAc/Petroleum ether 9:1. Pale yellow solid; mp 137-138° C.; $^1$H-NMR (200 MHz, DMSO-d$_6$): δ (ppm) 0.65 (t, 3H, J=7.2), 1.34 (s, 3H), 1.53 (s, 3H), 2.81 (bm, 2H), 4.55 (s, 1H), 5.40 (bs, 2H), 6.37 (m, 1H), 6.90 (m, 1H), 7 58 (bt, 1H), 7.71 (d, 1H, J=3.6), 8.23 (s, 1H), 8.39 (bs, 1H), 9.80 (bs, 1H), 10.50 (bs, 1H).

(3aS, 4S, 6R, 6aR)-6-[6-(N'-Benzoyl-hydrazino)-2-chloro-9H-purin-9-yl]-2,2-dimethyl-tetrahydrofuro[3,4-d][1,3]dioxole-4-carboxylic acid ethylamide (Compound 17a). The product is purified by crystallization with a mixture of EtOAc/Et$_2$O 1:2, White solid, 80% yield; mp 120° C.; $^1$H-NMR (200 MHz, DMSO-dr$_6$): δ (ppm) 0.70 (t, 3H, J=7.2), 1.35 (s, 3H), 1.53 (s, 3H), 2.90 (m, 2H), 4.57 (s, 1H), 5.38 (s, 2H), 6.36 (s, 1H), 7.55 (bt, 1H), 7.60 (m, 5H), 8.40 (s, 1H), 9.40 (bs, 1H), 10.66 (bs, 1H).

(3aS, 4S, 6R, 6aR)-6-{6-[N'-(Furan-2-carbonyl)-hydrazino]-2-chloro-9H-purin-9-yl}-2,2-dimethyl-tetrahydrofuro[3,4-d][1,3]dioxole-4-carboxylic acid ethylamide (Compound 18a). The product is purified by crystallization with EtOAc. White solid; mp 138-140° C.; $^1$H-NMR (200 MHz, DMSO-d$_6$): δ (ppm) 0.69 (t, 3H, J=7.2), 1.34 (s, 3H), 1.53 (s, 3H), 2.86 (m, 2H), 4.55 (bs, 1H), 5.37 (bs, 2H), 6.34 (bm, 1H), 6.70 (bs, 1H), 7.26 (bs, 1H), 7.60 (bt, 1H), 7.93 (bs, 1H), 8.40 (bs, 1H), 10.20 (bs, 1H), 10.80 (bs, 1H).

(3aS, 4S, 6R, 6aR)-2,2-Dimethyl-6-{6-[N'-(5-methyl-thiophene-2-carbonyl)-hydrazino]-2-chloro-9H-purin-9-yl}-tetrahydrofuro[3,4-d][1,3]dioxole-4-carboxylic acid ethylamide (Compound 19a) The product is purified by crystallization with a mixture of EtOAc/Et$_2$O 1:2. Pale yellow solid; mp 185° C.; $^1$H-NMR (200 MHz, DMSO-d$_6$): δ (ppm) 0.74 (t, 3H, J=7.2), 1.40 (s, 3H), 1.58 (s, 3H), 2.54 (s, 3H), 2.95 (bm, 2H), 4.63 (s, 1H), 5.40 (m, 1H), 5.58 (m, 1H), 6.33 (bs, 1H), 6.87 (d, 1H, J=3), 7.66 (d, 1H, J=3.6), 8.07 (bs, 1H), 8.21 (bs, 1H), 10.10 (bs, 1H), 10.80 (bs, 1H).

(3aS, 4S, 6R, 6aR)-6-{2-Chloro-6-[N'-(2-thiophen-2-yl-acetyl)-hydrazino]-9H-purin-9-yl}-2,2-dimethyl-tetrahydrofuro[3,4-d][1,3]dioxole-4-carboxylic acid ethylamide (Compound 20a). The product is purified by column chromatography on silica gel eluting with EtOAc. White solid; mp 118-119° C.; $^1$H-NMR (400 MHz, DMSO-d$_6$): δ (ppm) 0.68 (t, 3H, J=7.2), 1.34 (s, 3H), 1.53 (s, 3H), 2.80 (bm, 2H), 3.78 (s, 2H), 4.55 (m, 1H), 5 36 (s, 2H), 6.32 (s, 1H), 6.96 (bm, 2H), 7.37 (m, 1H), 7.60 (bt, 1H), 8.35 (s, 1H), 10.10-10.60 (bm, 2H).

(3aS, 4S, 6R, 6aR)-6-{2-Chloro-6[N'-(thiophene-3-carbonyl)-hydrazino]-9H-purin-9-yl}-2,2-dimethyl-tetrahydrofuro[3,4-d][1,3]dioxole-4-carboxylic acid ethylamide (Compound 21a). The product is purified by crystallization with a mixture of Et2O/Petroleum ether 1:2. White solid; mp 131-132° C.; $^1$H-NMR (400 MHz, DMSO-d$_6$): δ (ppm) 0.70 (t, 3H, J=7.2), 1.34 (s, 3H), 1.55 (s, 3H), 2.79 (bm, 2H), 4.55 (m, 1H), 5.39 (m, 2H), 6.40 (m, 1H), 7.53-7.71 (m, 2H), 8.21 (bm, 2H), 8.40 (bs, 1H), 10.20-11.00 (bm, 2H).

(3aS, 4S, 6R, 6aR)-6-{2-Chloro-6-[N'-(thiophene-2-carbonyl)-hydrazino]-9H-purin-9-yl}-2,2-dimethyl-tetrahydrofuro[3,4-d][1,3]dioxole-4-carboxylic acid ethylamide (Compound 22a). The product is purified by crystallization with a mixture of Et$_2$O/Petroleum ether 1:2. Pale yellow solid; mp 124-125° C.; $^1$H-NMR (400 MHz, DMSO-d$_6$): δ (ppm) 0.69 (t, 3H, J=7.2), 1.34 (s, 3H), 1.53 (s, 3H), 2.80 (bm, 2H), 4.54 (m, 1H), 5.38 (m, 2H), 6.33 (m, 1H), 7.23 (m, 1H), 7.61 (s, 1H), 7.90 (bm, 2H), 8.39 (bs; 1H), 10.10-10.90 (bm, 2H).

(3aS, 4S, 6R, 6aR)-6-{2-Chloro-6-[N'-(3-methyl-thiophene-2-carbonyl)-hydrazino]-9H-purin-9-yl)-2,2-dimethyl-tetrahydrofuro[3,4-d][1,3]dioxole-4-carboxylie acid ethylamide (Compound 23a). The product is purified by crystallization with a mixture of Et$_2$O/Petroleum ether 1:2. Pale yellow solid; mp 125° C.; $^1$H-NMR (400 MHz, DMSO-d$_6$): δ (ppm) 0.70 (t, 3H, J=7.2), 1.35 (s, 3H), 1.53 (s, 3H), 2.90 (bm, 2H), 4.56 (bs, 1H), 5.38 (bs, 2H), 6.34 (m, 1H), 7.02 (s, 1H), 7.61 (m, 2H), 8.39 (bs, 1H), 10.10-10.50 (bm, 2H).

(3aS, 4S, 6R, 6aR)-6-{2-Chloro-6-[N'-(1H-pyrrole-2-carbonyl)-hydrazino]-9H-purin-9-yl}-2,2-dimethyl-tetrahydrofuro[3,4-d][1,3]dioxole-4-carboxylic acid ethylamide (Compound 24a). The product is purified by crystallization with a mixture of Et$_2$O/Petroleum ether 1:2. Pale yellow solid; mp 147-148° C.; $^1$H-NMR (400 MHz, DMSO-d$_6$): δ (ppm) 0.70 (t, 3H, J=7.2), 1.35 (s, 3H), 1.53 (s, 3H), 2.90 (bm, 2H), 4.56 (s, 1H), 5.37 (bs, 2H), 6.15 (s, 1H), 6.35 (bs, 1H), 6.94 (s, 2H), 7.61 (s, 1H), 8.39 (bs, 1H), 10.10 (bm, 2H), 11.60 (bm, 1H).

(3aS, 4S, 6R, 6aR)-6-{2-Chloro-6-[N'-(5-methyl-isoxazole-3-carbonyl)-hydrazino]-9H-purin-9-yl}-2,2-dimethyl-tetrahydrofuro[3,4-d][1,3]dioxole-4-carboxylic acid ethylamide (Compound 25a) The product is purified by crystallization with a mixture of Et$_2$O/Petroleum ether 1:2. White solid; mp 150-151° C.; $^1$H-NMR (200 MHz, DMSO-d$_6$): δ (ppm) 0.67 (t, 3H, J=7.2), 1.34 (s, 3H), 1.55 (s, 3H), 2.44 (s, 3H), 2.87 (bm, 2H), 4.58 (s, 1H), 5.40 (bs, 2H), 6.25 (s, 1H), 7.61 (bm, 1H), 8.20 (s, 1H), 8.39 (bs, 1H), 10.20 (bm, 1H), 11.80 (bm, 1H).

(3aS, 4S, 6R, 6aR)-6-{2-Chloro-6-(N'-(5-phenyl-isoxazole-3-carbonyl)-hydrazino]-9H-purin-9-yl)-2,2-dimethyl-tetrahydrofuro[3,4-dl][1,3]dioxole4-carboxylic acid ethylamide (Compound 26a). The product is purified by crystallization with a mixture of Et$_2$O/Petroleum ether 1:2. White solid, 73% yield; mp 139-140° C.; $^1$H-NMR (200 MHz, DMSO-d$_6$): δ (ppm) 0.70 (t, 3H, J=7.2), 1.35 (s, 3H), 1.55 (s, 3H), 2.85 (bm, 2H), 4.55 (s, 1H), 5.40 (bs, 2H), 628 (s, 1H), 7.40-7.60 (m, 4H), 7.97 (m, 2H), 8.22 (s, 1H), 8.39 (bs, 1H), 10.20 (bm, 1H), 11.80 (bm, 1H).

EXAMPLE 3

Removal of the Isopropylidene Moiety (Compounds 9b-26b)

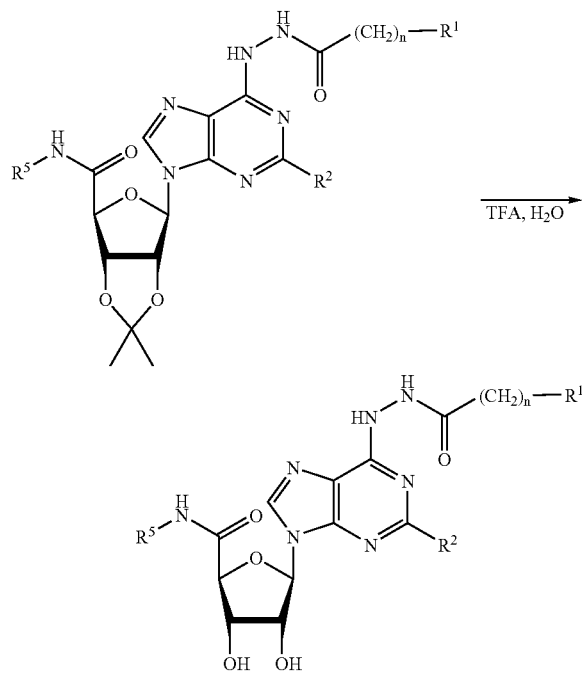

The isopropylidene derivatives (0.05 mmol) are dissolved in a mixture of TFA/water-1:1 (5 mL) and the resultant solution is stirred at room temperature for 3 hours, The solvent is evaporated under high vacuum and the residue purified by column chromatography with the appropriate mixture of ethyl acetate-methanol:

(2S, 3S, 4R, 5R)-5-[6-(N'-Benzoyl-hydrazino)-9H-purin-9-yl]-3,4-dihydroxy-tetrahydrofuran-2 carboxylic acid ethylamide (Compound 9b). The product is purified by column chromatography on silica gel eluting with EtOAc. White solid; mp 173-174° C.; $^1$H-NMR (200 MHz DMSO-d$_6$): δ (ppm) 1.07 (t, 3H, J=7.2), 3.21 (m, 2H), 4.17 (bs, 1H), 4.32 (s, 1H). 4.61 (bm, 1H), 5.61 (bm, 1H), 5.75 (bm, 1H), 6.00 (bm, 1H), 7.56 (m, 3H), 7.94 (m, 2H), 8.34 (s, 1H), 8.45 (bs, 1H), 8.74 (bt, 1H), 10.00 (bs, 1H), 10.60 (bs, 1H). Anal (C$_{19}$H$_{21}$N$_7$O$_5$) C, H, N.

(2S, 3S, 4R, 5R)-5-{6-[N'-(4-Chlorobenzoyl)-hydrazino]-9H-purin-9-yl}-3,4-dihydroxy-tetrahydrofuran-2-carboxylic acid ethylamide (Compound 10b) The product is purified by column chromatography on silica gel eluting with a mixture of CH$_2$Cl$_2$/CH$_3$OH 9.5:05. White solid; mp 188-190° C.; $^1$H-NMR (200 MHz, DMSO-d$_6$): δ (ppm) 1.10 (t, 3H, J=7.2), 3.17 (m, 2H), 4.02 (bm, 1H), 4.31 (m, 1H), 4.63 (bs, 1H), 4.68 (bm, 2H), 6.00 (d, 1H, J=7.3), 7.61 (d, 211, J=8), 7.96 (d, 2H, J=8), 8.34 (s, 1H), 8.51 (bs, 1H), 8.75 (bt, 1H), 10.00 (bs, 1H), 10.80(bs, 1H) Anal. (C$_{19}$H$_{20}$ClN$_7$O$_5$) C, H, N.

(2S, 3S, 4R, 5R)-3,4-Dihydroxy-5-{6-[N'-(pyridine-3-carbonyl)-hydrazino]-9H-purin-9-yl}-tetrahydrofuran-2-carboxylic acid ethylamide (Compound 11b). The product is purified by column chromatography on silica gel eluting with a mixture of EtOAc/CH$_3$OH 9:1. White solid; mp 170° C.; $^1$H-NMR (200 MHz, DMSO-d$_6$): δ (ppm) 1.07 (t, 3H, J=7.2), 3.20 (m, 2H), 4.15 (bs, 1H), 4.31 (s, 1H), 4.62 (bm, 1H), 5.62 (d, 1H, J=6.4), 5.76 (d, 1H, J=4.2), 6.00 (d, 1H, J=73),'58 (m, 1H), 8.30 (m, 1H), 8.35 (s, 1H), 8.54 (bs, 2H), 8.76 (m, 2H), 10.10 (bs, 1H), 11.00 (bs, 1H). Anal. (C$_{18}$H$_{20}$N$_8$O$_5$) C, H, N.

(2S, 3S, 4R, 5R)-5-{6-[N'-(Furan-2-carbonyl)-hydrazino]-9H-purin-9-yl}-3,4-dihydroxy-tetrahydrofuran-2-carboxylic acid ethylamide (Compound 12b). The product is purified by column chromatography on silica gel eluting with a mixture of EtOAc/CH$_3$OH 9.5:0.5. White solid; mp 233-234° C.; $^1$H-NMR (200 MHz, DMSO-d$_6$): δ (ppm) 1.10 (t, 3H, J=7.2), 3.20 (m, 2H), 4.08 (bs, 1H), 4.31 (s, 1H), 4.62 (bm, 1H), 5.62 (d, 1H, J=6.4), 5.76 (d, 1H, J=4.2), 6.00 (d, 1H, J=7.3), 6.68 (m, 1H), 7.26 (d, 1H, J=3.4), 7.93 (s, 1H), 8.44 (s, 1H), 8.54 (bs, 1H), 8.76 (bt, 1H), 9.97 (bs, 1H), 10.52 (bs, 1H). Anal. (C$_{17}$H$_{19}$N$_7$O$_6$) C, H, N.

(2S, 3S, 4R, 5R)-5-{6-[N'-(5-Bromo-furan-2-carbonyl)-hydrazino]-9H-purin-9-yl}-3,4-dihydroxy-tetrahydrofuran-2-carboxylic acid ethylamide (Compound 13b). The product is purified by column chromatography on silica gel eluting with a mixture of EtOAc/CH$_3$OH 9.5:0.5. White solid; mp 171° C.; $^1$H-NMR (200 MHz, DMSO-d$_6$): δ (ppm) 1.07 (t, 3H, J=7.2), 3.21 (m, 2H), 4.18 (bm, 1H), 4.32 (s, 1H), 4.65 (bm, 1H), 5.62 (d, 1H, J=6.2), 5,7 (d, 1H, J=4.4), 6.00 (d, 1H, J=7.6), 6.83 (d, 1H, J=3.4), 7.30 (d, 1H, J=3.4), 8.33 (s, 1H), 8.35 (bs, 1H), 8.74 (bt, 1H), 10.00 (bs, 1H), 10.60 (bs, 1H). Anal. (C$_{17}$H$_{18}$BrN$_7$O$_6$) C, H, N.

(2S, 3S, 4R, 5R)-3,4-Dihydroxy-5-{6-[N'-(5-methyl-furan-2-carbonyl)-hydrazino]-9H-purin-9-yl}-tetrahydrofuran-2-carboxylic acid ethylamide (Compound 14b) The product is purified by column chromatography on silica gel eluting with a mixture of EtOAc/CH$_3$OH 9.5:0.5. White solid; mp 154-156° C.; $^1$H-NMR (400 MHz, DMSO-d$_6$): δ (ppm) 1.07 (t, 3H, J=7.2), 2.37 (s, 3H), 3.21 (m, 2H), 4.16 (bs, 1H), 4.32 (bs, 1H), 4.62 (bs, 1H), 5.62 (d, 1H, J=6.4), 5.7 (d, 1H, J=4A), 6.00 (bm, 1H), 6.31 (m, 1H), 7.15 (m, 1H), 8.32 (s, 1H), 8.54 (bs, 1H), 8.76 (bt, 1H), 9.92 (bs, 1H), 10.31 (bs, 1H). Anal (C$_{18}$H$_{21}$N$_7$O$_6$) C, H, N.

(2S, 3S, 4R, 5R)-3,4-Dihydroxy-5-{6-[N'-(1-methyl-4-nitro-1H-imidazole-2-carbonyl)-hydrazino]-9H-purin-9-yl}-tetrahydrofuran-2-carboxylic acid ethylamide (Compound 15b). The product is purified by column chromatography on silica gel eluting with a mixture of EtOAc/CH$_3$OH 9:1. White solid; mp 168-170° C.; $^1$H-NMR (200 MHz, DMSO-d$_6$): δ (ppm) 1.07 (t, 3H, J=7.2), 3.20 (m, 2H), 3.99 (s, 3H), 4.15 (bm, 1H), 4.32 (bs, 1H), 4.63 (bm, 1N), 5.65 (bm, 1H), 5.76 (bs, 1H), 6.00 (d, 1H, J=7.6), 8.33 (s, 1H), 8.35 (bs, 1H), 8.65 (s, 1H), 8.74 (bt, 1H), 10.10-11.20 (bs, 2H). Anal. (C$_{17}$H$_{20}$N$_{10}$O$_7$) C, H, N.

(2S, 3S, 4R, 5R)-3,4-Dihydroxy-5-{6-[N'-(5-methyl-thiophene-2-carbonyl)-hydrazino]-9H-purin-9-yl}-tetrahydrofuran-2-carboxylic acid ethylamide (Compound 16b). The product is purified by column chromatography on silica gel eluting with a mixture of EtOAc/CH$_3$OH 9.5:0.5. White solid; mp 153-154° C.; $^1$H-NMR (200 MHz, DMSO-d$_6$): δ

(ppm) 1.06 (t, 3H, J=7.2), 3.16 (m, 2H), 3.20 (s, 3H), 4.13 (bm, 1H), 4.29 (bs, 1H), 4.61 (bm, 1H), 5.61 (bm, 1H), 5.74 (bm, 1H), 5.96 (d, 1H J=7.6), 6.86 (d, 1H, J=2.8), 7.67 (d, 1H, J=3.4), 8.28 (s, 1H), 8.44 (bs, 1H), 8.79 (bs, 1H), 10.00 (bs, 1H), 10.60 (bs. 1H). Anal. ($C_{18}H_{21}N_7O_5S$) C, H, N.

(2S, 3S, 4R, 5R)-5-[6{N'-Benzoyl-hydrazino)-2-chloro-9H-purin-9-yl]-3,4-dihydroxy-tetrahydrofuran-2-carboxylic acid ethylamide (Compound 17b). The product is purified with a mixture of EtOAc/Et$_2$O 1:2. White solid; mp 253-254° C.; $^1$H-NMR (200 MHz, DMSO-d$_6$): δ (ppm) 1.04 (t, 3H, J=7.2), 3.43 (m, 2H), 4.17 (bs, 1H), 4.32 (s, 1H), 4.58 (bs, 1H), 5.67 (bs, 2H), 5.96 (bm, 1H), 7.53 (m, 3H), 7.93 (m, 2H), 8.31 (bs, 1H), 8.63 (bt, 1H), 10.30 (bs, 1H), 10.90 (bs, 1H). Anal. ($C_{19}H_{20}ClN_7O_5$) C, H, N.

(2S, 3S, 4R, 5R)-5-{2-Chloro-6-[N'-(furan-2-carbonyl)-hydrazino]-9H-purin-9-yl}-3,4-dihydroxy-tetrahydrofuran-2-carboxylic acid ethylamide (Compound 18b). The product is purified by column chromatography on silica gel eluting with a mixture of EtOAc/CH$_3$OH 9.5:0.5. White solid; mp 268-270° C.; $^1$H-NMR (200 MHz, DMSO-d$_6$): δ (ppm) 1.04 (t, 3H, J=7.2), 3.21 (m, 2H), 4.20 (bs. 1H), 4.32 (bs, 1H), 4.60 (bs, 1H), 5.61 (bm, 1H), 5.75 (bm, 1H), 5.96 (bm, 1H), 6.71 (bs, 1H), 7.30 (bs, 1H), 7.94 (s, 1H), 8.34 (bs, 1H), 8.80 (bs, 1H), 10.00 (bs, 1H), 10.60 (bs, 1H). Anal ($C_{17}H_{18}ClN_7O_6$) C, H, N.

(2S, 3S, 4R, 5R)-5-{2-Chloro-6-[N'-(5-methyl-thiophene-2-carbonyl)-hydrazino]-9H-purin-9-yl}-3,4-dihydroxy-tetrahydrofuran-2-carboxylic acid ethylamide (Compound 19b). The product is purified by column chromatography on silica gel eluting with a mixture of EtOAc/CH$_3$OH 9.5:0.5. White solid; mp 156° C.; $^1$H-NMR (200 MHz, DMSO-d$_6$): δ (ppm) 1.04 (t, 3H, J=7.2), 3.20 (m, 2H), 4.16 (bs, 1H), 4.33 (bs, 1H), 4.61 (bs, 1H), 5.66 (bm, 1H), 5.78 (bm, 1H), 5.95 (bm, 1H), 6.71 (bs, 1H), 7.25 (bs, 1H), 8.40 (bs, 1H), 8.75 (bs, 1H), 10.00-11.00 (bm, 2H). Anal. ($C_{18}H_{20}ClN_7O_5S$) C, H, N.

(2S, 3S, 4R, 5R)-5-{2-Chloro-6-[N'-(2-thiophene-2-yl-acetyl)-hydrazino]-9H-purin-9-yl}-3,4-dihydroxy-tetrahydrofuran-2-carboxylic acid ethylamide (Compound 20b). The product is purified by column chromatography on silica gel eluting with a mixture of EtOAc/CH$_3$OH 9:1. White solid; mp 153-155° C.; $^1$H-NMR (200 MHz, DMSO-d$_6$): δ (ppm) 1.04 (t, 3H, J=7.2), 3.17 (m, 4H), 4.11 (bm, 1H), 4.31 (s, 1H), 4.57 (bm, 1H), 5.63-5.75 (m, 2H), 5.93 (m, 1H), 6.98 (m, 1H), 7.37 (m, 1H), 8.32 (bm, 2H), 8.56 (s, 1H), 10.00-11.00 (bm, 2H), Anal. ($C_{18}H_{20}ClN_7O_5S$) C, H, N.

(2S, 3S, 4R, 5R)-5-{2-Chloro-6-[N'-(thiophene-3-carbonyl)-hydrazino]-9H-purin-9-yl}-3,4-dihydroxy-tetrahydrofuran-2-carboxylic acid ethylamide (Compound 21b). The product is purified by column chromatography on silica gel eluting with a mixture of EtOAc/CH$_3$OH 9:1. White solid; mp 248-250° C.; $^1$H-NMR (200 MHz, DMSO-d$_6$): δ (ppm) 1.03 (t, 3H, J=7.2), 3.17 (m, 2H), 4.11 (bs, 1H), 4.32 (s, 1H), 4.57 (bm, 1H), 5.63-5.73 (m, 2H), 5.98 (m, 1H), 7.56-7.67 (m, 2H), 8.28 (bs, 2H), 8.62 (s, 1H), 10.00-11.00 (bm, 2H). Anal. ($C_{17}H_{18}ClN_7O_5S$) C, H, N.

(2S, 3S, 4R, 5R)-5-{2-Chloro-6-[N'-(thiophene-2-carbonyl)-hydrazino]-9H-purin-9-yl}3,4-dihydroxy-tetrahydrofuran-2-carboxylic acid ethylamide (Compound 22b). The product is purified by column chromatography on silica gel eluting with a mixture of EtOAc/CH$_3$OH 9:1. White solid; mp 189-190° C.; $^1$H-NMR (200 MHz, DMSO-d$_6$): δ (ppm) 1.05 (t, 3H, J=7.2), 3.21 (m, 2H), 4.18 (bs, 1H), 4.33 (s, 1H), 4.58 (bm, 1H), 5.65-5.75 (m, 2H), 5.95 (m, 1H), 7.24 (m, 1H), 7.87 (m, 2H), 8.33 (bs, 1H), 8.62 (s, 1H), 10.00-11.00 (bm, 2H). Anal. ($C_{17}H_{18}ClN_7O_5S$) C, H, N.

(2S, 3S, 4R, 5R)-5-{2-Chloro-6-[N'-(3-methyl-thiophene-2-carbonyl)-hydrazino-9H-purin-9-yl}-3,4-dihydroxy-tetrahydrofuran-2-carboxylic acid ethylamide (Compound 23b). The product is purified by column chromatography on silica gel eluting with a mixture of EtOAc/CH$_3$OH 9.5:0.5. White solid; mp 160-161° C.; $^1$H-NMR (200 MHz, DMSO-d$_6$): δ (ppm) 1.05 (t, 3H, J=7.2), 3.21 (m, 2H), 4.18 (bs, 1H), 4.32 (s, 1H), 4.58 (bm, 1H, 5.65-5.75 (m, 2H), 5.95 (m, 1H), 7.04 (d, 1H, J=4.6), 7.66 (d, 1H, J=4.8), 8.33 (bs, 1H), 8.61 (s, 1H), 10.00-10.60 (bm, 2H). Anal. ($C_{18}H_{20}ClN_7O_5S$) C, H, N.

(2S, 3S, 4R, 5R)-5-{2-Chloro-6-[N'-(1H-pyrrole-2-carbonyl)-hydrazino]-9H-purin-9-yl}-3,4-dihydroxy-tetrahydrofuran-2-carboxylic acid ethylamide (Compound 24b). The product is purified by column chromatography on silica gel eluting with a mixture of EtOAc/CH$_3$OH 9.5:0.5. White solid; mp 230-231° C.; $^1$H-NMR (200 MHz, DMSO-d$_6$): δ (ppm) 1.04 (t, 3H, J=7.2), 3.21 (m, 2H), 4.17 (bs, 1H), 4.32 (s, 1H), 4.57 (bm, 1H), 5.65 (m, 1H), 5.76 (s, 1H), 5.96 (m, 1H), 6.16 (s, 1H), 6.94 (bs, 2H), 8.34 (bm, 1H), 8 58 (s. 1H), 10.00-10.60 (bm, 2H), 11.65 (bm, 1H) Anal. ($C_{17}H_{19}ClN_8O_5$) C, H, N.

(2S, 3S, 4R, 5R)-5-{2-Chloro-6-[N'-(5-methyl-isoxazole-3-carbonyl)-hydrazino]-9H-purin-9-yl}-3,4-dihydroxy-tetrahydrofuran-2-carboxylic acid ethylamide (Compound 25b). The product is purified by column chromatography on silica gel eluting with a mixture of EtOAc/CH$_3$OH 9.5:0.5. White solid; mp 182-183° C.; $^1$H-NMR (200 MHz, DMSO-d$_6$): δ (ppm) 1.04 (t, 3H, J=7.2), 2.28 (s, 3H), 3.21 (m, 2H), 4.17 (bs, 1H), 4.32 (bs, 1H), 4.57 (bs, 1H), 5.61 (bm, 1H), 5.73 (bm, 1H), 5.96 (bm, 1H), 6.45 (bs, 1H), 8.31-8.60 (m, 2H), 10.00-10.50 (bm, 2H). Anal. ($C_{17}H_{19}ClN_8O_6$) C, H, N.

(2S, 3S, 4R, 5R)-5-{2-Chloro-6-[N'-(5-phenyl-isoxazole-3-carbonyl)-hydrazino]-9H-purin-9-yl}-3,4-dihydroxy-tetrahydrofuran-2-carboxylic acid ethylamide (Compound 26b). The product is purified by column chromatography on silica gel eluting with a mixture of EtOAc/CH$_3$OH 9.5:0.5 White solid; mp 169-170° C.; $^1$H-NMR (200 MHz, DMSO-d$_6$): δ (ppm) 1.05 (t, 3H, J=7.2), 3.20 (m, 2H), 4.19 (bs, 1H), 4.33 (s, 1H), 4.60 (bs, 1H), 5.65 (bs, 1H), 5.75 (bs, 1H), 5.96 (bm, 1H), 7.40-7.60 (m, 4H), 7.97 (m, 2H), 8.32 (bs, 1H), 8.64 (s, 1H), 10.00-11.00 (bs, 2H). Anal. ($C_{22}H_{21}ClN_8O_6$) C, H, N.

What is claimed is:
1. A compound of the formula

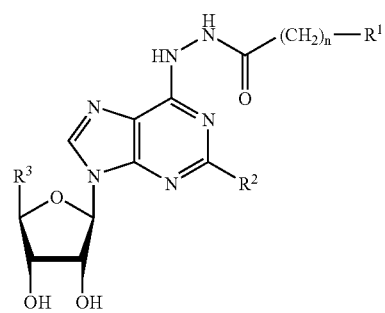

wherein
R$^1$ is an optionally substituted aryl or heteroaryl;
n is zero or 1;
R$^2$ is H or halogen;
R$^3$ is CH$_2$OR$^4$ in which
R$^4$ is H or C$_1$-C$_6$ alkyl provided that R$^4$ is not H when n is zero and R$^1$ is unsubstituted phenyl; or
R$^3$ is C(O)NH—R$^5$ in which
R$^5$ is C$_1$-C$_6$ alkyl; or

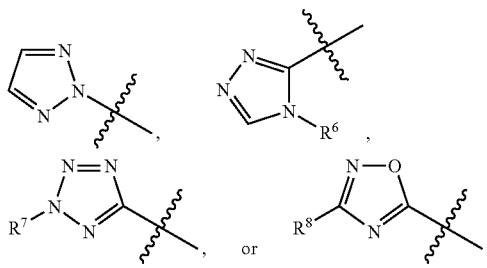

R³ is
in which
R⁶, R⁷, and R⁸ are H or $C_1$-$C_6$ alkyl;
or a pharmaceutically acceptable salt thereof; and wherein optionally substituted aryl refers to an unsaturated aromatic carbocyclic group of from 6 to 14 carbon atoms having a single ring or multiple condensed rings which may be optionally substituted with from 1 to 3 substituents selected from the group consisting of hydroxy, acyl, alkyl, alkoxy, alkylthio, alkenyl, alkynyl, amino, acyloxy, acylamino, aryl, aralkyl, aryloxy, azido, carboxy, cyano, halo, nitro, heteroaryl, heteroaryloxy, trihalomethoxy, dihalomethyl, trihalomethyl and perhaloalkyl; and optionally substituted heteroaryl refers to an unsaturated aromatic heterocyclic group having a single ring or multiple condensed rings, from 1 to 15 carbon atoms and from 1 to 4 hetero atoms selected from the group consisting of nitrogen, sulfur and oxygen within the ring, and which may be optionally substituted with from 1 to 3 substituents selected from the group consisting of hydroxy, acyl, alkyl, alkoxy, alkylthio alkenyl, alkynyl, amino, acyloxy, acylamino, aralkyl, aryloxy, azido, carboxy, cyano, halo, nitro, heteroaryl, heteroaryloxy, trihalomethoxy, dihalomethyl, perhaloalkyl and trihalomethyl.

2. A compound according to claim 1, wherein
R¹ is an optionally substituted furanyl;
or a pharmaceutically acceptable salt thereof.

3. A compound according to claim 2, wherein
R³ is C(O)NH—R⁵ in which
R⁵ is $C_1$-$C_6$ alkyl;
or a pharmaceutically acceptable salt thereof.

4. A compound according to claim 3 which is selected from the group consisting of:
(2S, 3S, 4R, 5R)-5-{6-[N'-(furan-2-carbonyl)-hydrazino]-9H-purin-9-yl}-3,4-dihydroxy-tetrahydrofuran-2-carboxylic acid ethylamide;
(2S, 3S) 4R, 5R)-5-{6-[N'-(5-bromo-furan-2-carbonyl)-hydrazino]-9H-purin-9-yl}-3,4-dihydroxy-tetrahydrofuran-2-carboxylic acid ethylamide;
(2S, 3S, 4R, 5R)-3,4-dihydroxy-5-{6-[N'-(5-methyl-furan-2-carbonyl)-hydrazino]-9H-purin-9-yl}-tetrahydrofuran-2-carboxylic acid ethylamide; and
(2S, 3S, 4R, 5R)-5-{2-chloro-6-[N'-(furan-2-carbonyl)-hydrazino]-9H-purin-9-yl}-3,4-dihydroxy-tetrahydrofuran-2-carboxylic acid ethylamide;
or a pharmaceutically acceptable salt thereof.

5. A compound according to claim 1, wherein
R¹ is an optionally substituted thienyl;
or a pharmaceutically acceptable salt thereof.

6. A compound according to claim 5, wherein
R³ is C(O)NH—R⁵ in which
R⁵ is $C_1$-$C_6$ alkyl:
or a pharmaceutically acceptable salt thereof.

7. A compound according to claim 6 which is selected from the group consisting of:
(2S, 3S, 4R, 5R)-3,4-dihydroxy-5-{6-[N'-(5-methyl-thiophene-2-carbonyl)-hydrazino]-9H-purin-9-yl}-tetrahydrofuran-2-carboxylic acid ethylamide;
(2S, 3S, 4R, 5R)-5-{2-chloro-6-[N'-(5-methyl-thiophene-2-carbonyl)-hydrazino]-9H-purin-9-yl}-3,4-dihydroxy-tetrahydrofuran-2-carboxylic acid ethylamide;
(2S, 3S, 4R, 5R)-5-{2-chloro-6-[N'-(thiophene-3-carbonyl)-hydrazino]-9H-purin-9-yl}-3,4-dihydroxy-tetrahydrofuran-2-carboxylic acid ethylamide;
(2S, 3S, 4R, 5R)-5-{2-chloro-6-[N'-(thiophene-2-carbonyl)-hydrazino]-9H-purin-9-yl}3,4-dihydroxy-tetrahydrofuran-2-carboxylic acid ethylamide;
(2S, 3S, 4R, 5R)-5-{2-chloro-6-[N'-(3-methyl-thiophene-2-carbonyl)-hydrazino]-9H-purin-9-yl}-3,4-dihydroxy-tetrahydrofuran-2-carboxylic acid ethylamide; and
(2S, 3S, 4R, 5R)-5-{2-chloro-6-[N'-(2-thiophene-2-ylacetyl)-hydrazino]-9H-purin-9-yl}-3,4-dihydroxy-tetrahydrofuran-2-carboxylic acid ethylamide;
or a pharmaceutically acceptable salt thereof.

8. A compound according to claim 1, wherein
R¹ is an optionally substituted monocyclic aryl or heteroaryl;
or a pharmaceutically acceptable salt thereof.

9. A compound according to claim 8, wherein
R³ is C(O)NH—R⁵ in which
R⁵ is $C_1$-$C_6$ alkyl;
or a pharmaceutically acceptable salt thereof.

10. A compound according to claim 8 which is selected from the group consisting of:
(2S, 3S, 4R, 5R)-5-[6-(N'-benzoyl-hydrazino)-9H-purin-9-yl]-3,4-dihydroxy-tetrahydrofuran-2 carboxylic acid ethylamide;
(2S, 3S, 4R, 5R)-5-{6-[N'-(4-chloro-benzoyl)-hydrazino]-9H-purin-9-yl}-3,4-dihydroxy-tetrahydrofuran-2-carboxylic acid ethylamide;
(2S, 3S, 4R, 5R)-3,4-dihydroxy-5-{6-[N'-(pyridine-3-carbonyl)-hydrazino]-9H-purin-9-yl}-tetrahydrofuran-2-carboxylic acid ethylamide;
(2S, 3S, 4R, 5R)-3,4-dihydroxy-5-{6-[N'-(1-methyl-4-nitro-1H-imidazole-2-carbonyl)-hydrazino]-9H-purin-9-yl}-tetrahydrofuran-2-carboxylic acid ethylamide;
(2S, 3S, 4R, 5R)-5-[6-{N'-benzoyl-hydrazino)-2-chloro-9H-purin-9-yl}-3,4-dihydroxy-tetrahydrofuran-2-carboxylic acid ethylamide;
(2S, 3S, 4R, 5R)-5-{2-chloro-6-[N'-(1H-pyrrole-2-carbonyl)-hydrazino]-9H-purin-9-yl}-3,4-dihydroxy-tetrahydrofuran-2-carboxylic acid ethylamide;
(2S, 3S, 4R, 5R)-5-{2-chloro-6-[N'-(5-methyl-isoxazole-3-carbonyl)-hydrazino]-9H-purin-9-yl}-3,4-dihydroxy-tetrahydrofuran-2-carboxylic acid ethylamide; and
(2S, 3S, 4R, 5R)-5-{2-chloro-6-[N'-(5-phenyl-isoxazole-3-carbonyl)-hydrazino]-9H-purin-9-yl}-3,4-dihydroxy-tetrahydrofuran-2-carboxylic acid ethylamide;
or a pharmaceutically acceptable salt thereof.

11. A pharmaceutical composition comprising a therapeutically effective amount of a compound of claim 1 in combination with one or more pharmaceutically acceptable carriers.

* * * * *

UNITED STATES PATENT AND TRADEMARK OFFICE
CERTIFICATE OF CORRECTION

PATENT NO. : 7,691,825 B2
APPLICATION NO. : 11/757559
DATED : April 6, 2010
INVENTOR(S) : Baraldi et al.

It is certified that error appears in the above-identified patent and that said Letters Patent is hereby corrected as shown below:

Column 10, line 18; Columns 11-12, line 17 (Table 1); column 16, lines 45, 54 and 64; column 17, lines 5, 26 and 58; column 18, line 3; column 19, lines 52 and 64; column 20, lines 44, 55 and 66; column 21, lines 8, 19, 29, 39, 49, 58 and 67; column 22, lines 10, 20, 30, 39, 48, 57 and 66; column 23, lines 9 and 59; column 24, lines 2, 12, 22, 34, 45, 56 and 67; column 25, lines 10, 20, 31, 41, 51 and 61; column 26, lines 4, 14, 25 and 35; in each instance, "C." should be changed to --C--.

Column 19, line 50, "9.8:9.2" should be changed to --9.8:0.2--.

Column 22, line 29, "Et2O" should be changed to --Et$_2$O--.

Column 23, line 11, "628" should be changed to --6.28--.

Column 24, line 2, "9.5:05" should be changed to --9.5:0.5--.

Column 24, line 15, "J=73" should be changed to --J=7.3--.

Column 24, line 15, "'58" should be changed to --7.58--.

Signed and Sealed this

Sixth Day of July, 2010

David J. Kappos
*Director of the United States Patent and Trademark Office*